United States Patent
Khanna et al.

(10) Patent No.: US 11,875,124 B2
(45) Date of Patent: Jan. 16, 2024

(54) VIRTUAL ASSISTANT FOR A PHARMACEUTICAL ARTICLE

(71) Applicant: ACTO Technologies Inc., Toronto (CA)

(72) Inventors: Parth Khanna, Toronto (CA); Kumar Karthik Erramilli, Pickering (CA); Kapil Kalra, Mississauga (CA)

(73) Assignee: ACTO Technologies Inc., Toronto (CA)

(*) Notice: Subject to any disclaimer, the term of this patent is extended or adjusted under 35 U.S.C. 154(b) by 128 days.

(21) Appl. No.: 17/170,002

(22) Filed: Feb. 8, 2021

(65) Prior Publication Data
US 2022/0253608 A1    Aug. 11, 2022

(51) Int. Cl.
G06F 40/35   (2020.01)
G06F 40/295  (2020.01)
G16H 20/10   (2018.01)
G06N 20/00   (2019.01)
H04W 4/021   (2018.01)

(52) U.S. Cl.
CPC ............ *G06F 40/35* (2020.01); *G06F 40/295* (2020.01); *G06N 20/00* (2019.01); *G16H 20/10* (2018.01); *H04W 4/021* (2013.01)

(58) Field of Classification Search
CPC ....... G06F 40/35; G06F 40/295; G06N 20/00; G06N 20/10; H04W 4/021
See application file for complete search history.

(56) References Cited

U.S. PATENT DOCUMENTS

| | | | |
|---|---|---|---|
| 7,483,871 B2 * | 1/2009 | Herz | H04N 21/4332 |
| 9,881,077 B1 * | 1/2018 | Alfonseca | G06F 16/35 |
| 2007/0106754 A1 * | 5/2007 | Moore | G16H 40/20 |
| | | | 707/E17.116 |
| 2014/0258863 A1 * | 9/2014 | Woods | G06F 3/0484 |
| | | | 715/716 |
| 2014/0365468 A1 * | 12/2014 | Ormont | G06F 16/2455 |
| | | | 707/722 |
| 2015/0205868 A1 * | 7/2015 | Boncyk | G06Q 30/0269 |
| | | | 707/722 |
| 2019/0026328 A1 * | 1/2019 | Jin | G06Q 10/0635 |

(Continued)

*Primary Examiner* — Anne L Thomas-Homescu
(74) *Attorney, Agent, or Firm* — Fernando & Partners, LLP

(57) ABSTRACT

Various implementations disclosed herein include devices, systems, and methods for providing domain-specific responses. In various implementations, a device includes a non-transitory memory and a processor coupled with the non-transitory memory. In some implementations, a method includes determining a user interest value indicative of a pharmaceutical article that the user is interested in learning about. In some implementations, the pharmaceutical article is associated with a set of media content items that provide information regarding the pharmaceutical article. In some implementations, the method includes setting a configuration parameter of a virtual agent to a configuration value that is based on the pharmaceutical article indicated by the user interest value. In some implementations, the method includes after setting the configuration parameter of the virtual agent, generating, by the virtual agent, a response to a query based on the information provided by the set of media content items associated with the pharmaceutical article.

23 Claims, 12 Drawing Sheets

(56) References Cited

U.S. PATENT DOCUMENTS

| | | | |
|---|---|---|---|
| 2020/0013516 A1* | 1/2020 | Ito | G06N 5/022 |
| 2021/0081503 A1* | 3/2021 | Tran | G06K 9/6215 |
| 2021/0233650 A1* | 7/2021 | Parab | G16H 40/20 |

* cited by examiner

VIRTUAL ASSISTANT FOR A PHARMACEUTICAL ARTICLE

TECHNICAL FIELD

The present disclosure generally relates to a virtual assistant that provides information regarding a pharmaceutical article.

BACKGROUND

Some devices are capable of performing a task for a person in response to receiving a command from the person. Some devices are capable of providing an answer to a question in response to receiving the question from a person. Some devices receive the command or the question in the form of a textual input. Some devices receive the command or the question in the form of a voice input. Some devices provide the answer to the question as a voice output. Some devices provide the answer to the question as a textual output.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

Figure 1A:
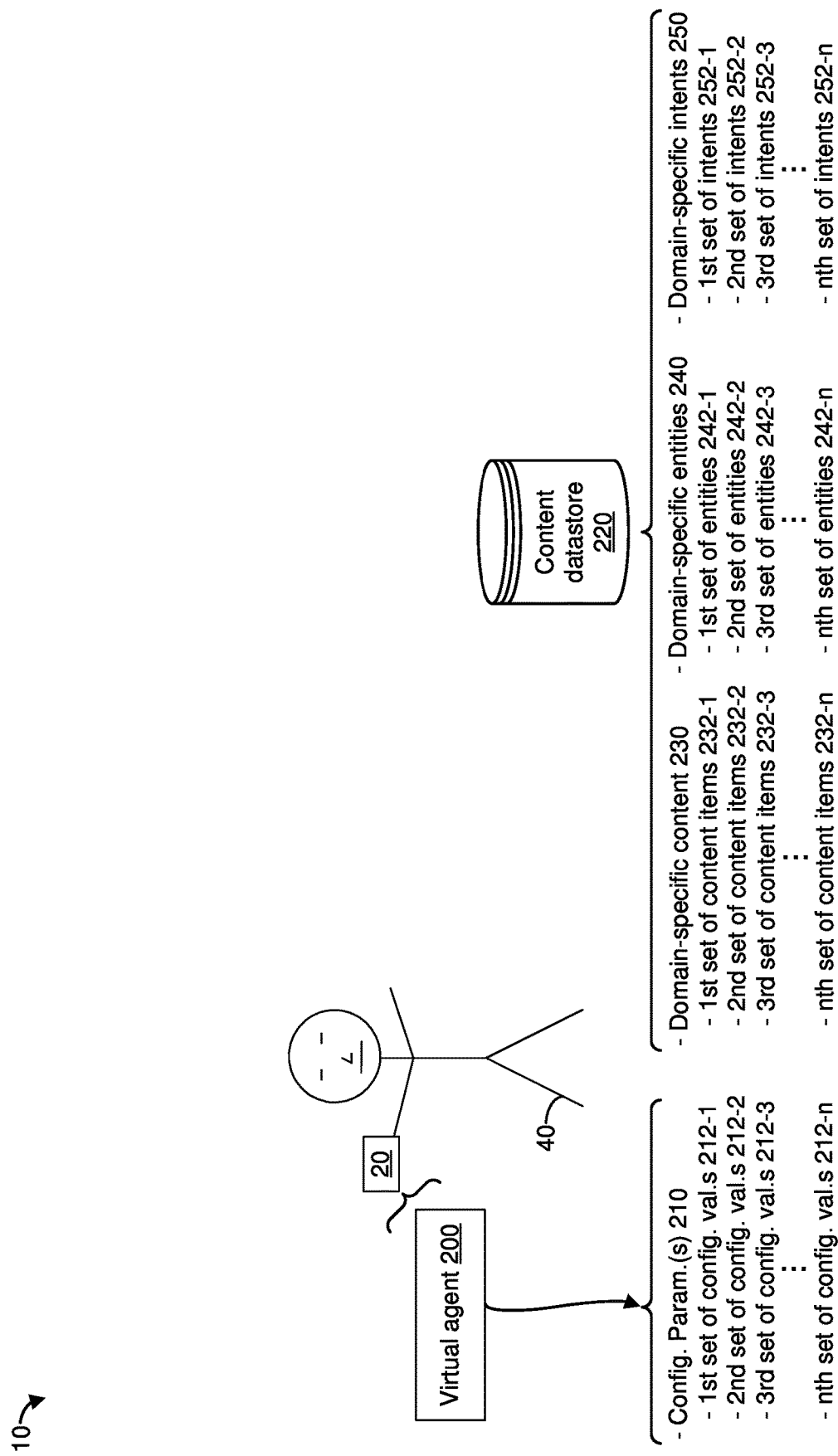
FIGS. 1A-1I are diagrams of an example operating environment in accordance with some implementations.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

SUMMARY

Various implementations disclosed herein include devices, systems, and methods for providing domain-specific responses. In various implementations, a device includes a non-transitory memory and a processor coupled with the non-transitory memory. In some implementations, a method includes determining a user interest value indicative of a pharmaceutical article that the user is interested in learning about. In some implementations, the pharmaceutical article is associated with a set of media content items that provide information regarding the pharmaceutical article. In some implementations, the method includes setting a configuration parameter of a virtual agent to a configuration value that is based on the pharmaceutical article indicated by the user interest value. In some implementations, the method includes after setting the configuration parameter of the virtual agent, generating, by the virtual agent, a response to a query based on the information provided by the set of media content items associated with the pharmaceutical article.

In accordance with some implementations, a device includes one or more processors, a non-transitory memory, and one or more programs. In some implementations, the one or more programs are stored in the non-transitory memory and are executed by the one or more processors. In some implementations, the one or more programs include instructions for performing or causing performance of any of the methods described herein. In accordance with some implementations, a non-transitory computer readable storage medium has stored therein instructions that, when executed by one or more processors of a device, cause the device to perform or cause performance of any of the methods described herein. In accordance with some implementations, a device includes one or more processors, a non-transitory memory, and means for performing or causing performance of any of the methods described herein.

DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects and/or variants do not include all of the specific details described herein. Moreover, well-known systems, methods, components, devices, and circuits have not been described in exhaustive detail so as not to obscure more pertinent aspects of the example implementations described herein.

Some devices that provide voice search cover a variety of domains or subjects in an effort to provide a user with answers to questions that relate to a variety of domains. For example, some devices implement a virtual assistant that may be trained to provide answers to queries that relate a wide range of domains including sports, world news, music, entertainment, etc. However, the breadth of domains can lead to a lack of depth in a particular domain that the user is interested in learning about. Moreover, since a particular user query may be relevant to several domains, the user often has to provide queries with a relatively high degree of specificity in order to allow the device to disambiguate the query, determine which domain the query is related to and generate a domain-specific response to the query.

The present disclosure provides methods, systems and/or devices for providing domain-specific (e.g., subject-specific) voice search capability to a user based on a domain (e.g., subject) that the user is interested in learning about. The device obtains contextual data indicating a particular domain that the user is interested in learning about. After determining that the user is interested in learning about a particular domain, the device configures a virtual assistant to provide answers to user queries from information that is related to that particular domain Configuring the virtual assistant based on the domain that the user is interested in learning about results in transforming the virtual assistant from a domain-agnostic virtual assistant (e.g., a generic virtual assistant) to a domain-specific virtual assistant. As such, while the user is interested in learning about that particular domain, the virtual assistant may be provided access to information pertaining to that particular domain and the virtual assistant may not be provided access to information related to other domains that the user is not interested in learning about.

Configuring the virtual assistant to operate as a domain-specific virtual assistant enhances operability of the device by reducing an amount of resources associated with generating responses to user queries. For example, configuring the virtual assistant to operate as a domain-specific virtual assistant allows the virtual assistant to utilize a domain-specific vocabulary that includes a set of entities that are specific to that domain in order to disambiguate a query in a reduced amount of time. As another example, configuring the virtual assistant to operate as a domain-specific virtual assistant allows the virtual assistant to use fewer computing resources to identify entities referenced by a query because the virtual assistant compares phrases in the query with a domain-specific vocabulary that includes fewer entities than a domain-agnostic vocabulary (e.g., a generic glossary) that may include entities that relate to a variety of domains.

Configuring the virtual assistant to operate as a domain-specific virtual assistant enhances a user experience of the device by allowing the user to provide a shorter query or a query with less specificity. For example, the query need not specifically refer to the domain. As an example, if the virtual assistant is configured to provide dosage information for a variety of pharmaceutical drugs, the user may have to specify the pharmaceutical drug as part of the query. For example, if the virtual assistant is configured to provide dosage information for dapagliflozin, insulin and atorvastatin, and the user is interested in obtaining dosage information for dapagliflozin, the user may have to say "dosage information for dapagliflozin". However, if the virtual assistant is temporarily configured to provide information for dapagliflozin and no other pharmaceutical drugs, the user can say "dosage information" without specifying the name of the pharmaceutical drug. Processing shorter user inputs (e.g., shorter voice commands) may conserve computing resources thereby enhancing operability of the device.

The device can determine which domain the user is interested in learning about based on calendar event data stored in a calendar application. For example, if the device detects that an upcoming calendar event or a current calendar event relates to a particular domain, the device may determine that the user is more likely to ask questions pertaining to the particular domain related to the upcoming or current calendar event. As such, the device configures the virtual assistant so as to transform the virtual assistant from a generic virtual assistant or a multidomain virtual assistant to a domain-specific virtual assistant until the event ends.

The device can determine which domain the user is interested in learning about based on profile data. For example, if the device detects that the user has a profile that is associated with a particular domain, the device may determine that the user is more likely to ask questions pertaining to the particular domain indicated in the profile. As such, the device configures the virtual assistant so as to transform the virtual assistant from a generic virtual assistant to a domain-specific virtual assistant that generates responses based on information related to the domain indicated by the profile. If the profile indicates multiple domains, the device configures the virtual assistant to generate responses for each of the domains indicated by the profile.

The device can configure the virtual assistant to generate responses that are related to a particular domain by training the virtual assistant based on media content items that provide information related to the particular domain. The device configures the virtual assistant to generate responses using a corpus of information that relates to that particular domain. The device can configure the virtual assistant by loading a model that has been trained with training data that relates to that particular domain. The virtual assistant may include a neural network system with various neural network weights, and configuring the virtual assistant may include setting values of the neural network weights based on the domain that the user is interested in learning about.

FIG. 1A is a diagram of an example operating environment 10 in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the operating environment 10 includes an electronic device 20 ("device 20", hereinafter for the sake of brevity), a user 40 of the device 20, a virtual agent 200 and a content datastore 220. As shown in FIG. 1A, in some implementations, the device 20 implements the virtual agent 200. Although the virtual agent 200 is shown as being integrated into the device 20, in some implementations, the virtual agent 200 is separate from the device 20. For example, in some implementations, at least a portion of the virtual agent 200 resides at (e.g., is implemented by) a remote device (e.g., a server or a cloud computing platform). In some implementations, the virtual agent 200 is referred to as a virtual assistant, a voice assistant or a voice-enabled assistant. Although the content datastore 220 is shown as being separate from the device 20 and the virtual agent 200, in some implementations, the content datastore 220 is integrated into the device 20 and/or the virtual agent 200. In some implementations, the user 40 includes a medical representative that represents a pharmaceutical article (e.g., the user 40 is responsible for informing healthcare providers about the pharmaceutical article that the user 40 represents), and the device 20 is referred to as a medical representative device.

In some implementations, the device 20 includes a handheld computing device that can be held by the user 40. For example, in some implementations, the device 20 includes a smartphone, a tablet, a media player, a laptop, or the like. In some implementations, the device 20 includes a wearable computing device that can be worn by the user 40. For example, in some implementations, the device 20 includes an electronic watch or a pair of headphones.

In various implementations, the virtual agent 200 provides responses to queries that the user 40 inputs into the device 20. For example, the user 40 may provide a voice query that the device 20 detects, and the virtual agent 200 generates a response to the voice query and outputs the response via a speaker of the device 20. The virtual agent 200 may be capable of providing responses to queries that relate to a variety of domains or subjects. However, in order to reduce the utilization of resources by the virtual agent 200, the virtual agent 200 is configured to provide responses to queries that relate to a particular domain or a subset of domains that the virtual agent can be configured to generate responses for.

The virtual agent 200 includes a set of one or more configuration parameters 210 ("configuration parameters 210", hereinafter for the sake of brevity). Setting the configuration parameters 210 to a particular set of configuration values causes the virtual agent 200 to be transformed into a domain-specific virtual agent. For example, setting the configuration parameters 210 to a first set of candidate configuration values 212-1 causes the virtual agent 200 to be transformed into a domain-specific virtual agent that provides responses to queries that relate to a first domain.

Similarly, setting the configuration parameters 210 to a second set of candidate configuration values 212-2 causes the virtual agent 200 to be transformed into a domain-specific virtual agent that provides responses to queries that relate to a second domain that is different from the first domain. As another example, setting the configuration parameters 210 to a third set of candidate configuration values 212-3 causes the virtual agent 200 to be transformed into a domain-specific virtual agent that provides responses to queries that relate to a third domain that is different from the first and second domains. As yet another example, setting the configuration parameters 210 to an nth set of candidate configuration values 212-n causes the virtual agent 200 to be transformed into a domain-specific virtual agent that provides responses to queries related to an nth domain that is different from the other domains.

In various implementations, different domains correspond to different articles (e.g., physical articles such as pharmaceutical articles, for example, pharmaceutical drugs or medical devices). For example, in some implementations, the first domain provides information regarding a medical device (e.g., an insulin delivery device such as an insulin pump). In some implementations, the second domain provides information regarding a pharmaceutical drug that treats a cardiac condition. For example, the second domain may provide information regarding a cholesterol-reducing drug such as atorvastatin. In some implementations, the third domain provides information regarding a pharmaceutical drug that treats an endocrinological disease or disorder. For example, the third domain may provide information regarding a blood glucose reducing drug such as dapagliflozin.

The content datastore 220 stores information regarding various domains. In various implementations, the content datastore 220 stores domain-specific content 230 for a variety of domains. As shown in FIG. 1A, in some implementations, the content datastore 220 stores a first set of content items 232-1 that provides information regarding a first domain (e.g., a medical device such as an insulin pump), a second set of content items 232-2 that provides information regarding a second domain (e.g., a first pharmaceutical drug, for example, a cholesterol-reducing drug such as atorvastatin), a third set of content items 232-3 that provides information regarding a third domain (e.g., a second pharmaceutical drug, for example, a blood glucose reducing drug such as dapagliflozin), . . . , and an nth set of content items 232-n that provides information regarding an nth domain. In various implementations, the content items include documents such as word documents or PDFs, audio content such as podcasts, video content such as documentaries or advertisements and textual content such as product labels of pharmaceutical drugs approved by a regulatory agency such as the Food and Drug Administration (FDA).

In various implementations, the content datastore 220 includes a relational database that stores information provided by the domain-specific content 230 in a structured form (e.g., as structured data). In various implementations, the domain-specific content 230 includes unstructured data that is not organized into specific data fields. In various implementations, a device (e.g., the device 20 or a server) converts the unstructured data in the domain-specific content 230 into structured data. For example, in some implementations, the device (e.g., the device 20 or the server) extracts information from the domain-specific content 230 and stores at least a portion of the information into specific data fields thereby making the information more accessible (e.g., searchable).

In various implementations, the content datastore 220 stores domain-specific entities 240. In some implementations, a device (e.g., the device 20 or a server) extracts the domain-specific entities 240 from content items that relate to a corresponding domain. For example, in some implementations, the domain-specific entities 240 include a first set of entities 242-1 that is extracted from the first set of content items 232-1, a second set of entities 242-2 that is extracted from the second set of content items 232-2, a third set of entities 242-3 that is extracted from the third set of content items 232-3, . . . , and an nth set of entities 242-n that is extracted from the nth set of content items 232-n. In various implementations, the sets of entities are different from each other because each set of entities is specific to a domain. For example, if the second domain relates to dapagliflozin and the third domain relates to an insulin pump, the second set of entities 242-2 may be specific to dapagliflozin and the third set of entities 242-3 may be specific to the insulin pump.

In some implementations, each set of domain-specific entities 240 forms a domain-specific vocabulary (e.g., a domain-specific glossary or a domain-specific dictionary). For example, the first set of entities 242-1 collectively forms a first domain-specific vocabulary that includes various phrases that are related to the insulin delivery device. As another example, the second set of entities 242-2 collectively forms a second domain-specific vocabulary that includes various phrases that are related to the cholesterol-reducing drug. As yet another example, the third set of entities 242-3 collectively forms a third domain-specific vocabulary that includes various phrases that are related to the blood glucose reducing drug.

In various implementations, the content datastore 220 includes a set of domain-specific intents 250. In some implementations, a device (e.g., the device 20 or a server) extracts the domain-specific intents 250 from the domain-specific content 230. In some implementations, a device determines the domain-specific intents 250 based on the domain-specific content 230 and/or the domain-specific entities 240. Alternatively or additionally, in some implementations, an operator (e.g., a human operator) specifies the domain-specific intents 250. The domain-specific intents 250 include a first set of intents 252-1 for the first domain (e.g., the insulin pump), a second set of intents 252-2 for the second domain (e.g., the cholesterol-reducing drug), a third set of intents 252-3 for the third domain (e.g., the blood glucose reducing drug), . . . , and an nth set of intents 252-n for the nth domain. In some implementations, the sets of intents are different from each other. For example, the second set of intents 252-2 related to the cholesterol-reducing drug may be different from the third set of intents 252-3 related to the blood glucose reducing drug.

In some implementations, each set of domain-specific intents 250 includes domain-specific queries (e.g., domain-specific questions) that the user 40 is likely to ask regarding the corresponding domain. For example, the first set of intents 252-1 includes a first set of queries that the user 40 is likely to ask regarding the insulin pump. As another example, the second set of intents 252-2 includes a second set of queries that the user 40 is likely to ask regarding cholesterol-reducing drug. As yet another example, the third set of intents 252-3 includes a third set of queries that the user 40 is likely to ask regarding the blood glucose reducing drug.

In various implementations, the sets of candidate configuration values 212-1, 212-2, 212-3, . . . , and 212-n are associated with a respective one of the sets of content items 232-1, 232-2, 232-3, . . . , and 232-n, a respective one of the sets of entities 242-1, 242-2, 242-3, . . . , and 242-n, and a respective one of the sets of intents 252-1, 252-2, 252-3, . . . , and 252-n. For example, the first set of candidate configuration values 212-1 is associated with the first set of content items 232-1, the first set of entities 242-1 and the first set of intents 252-1. As another example, the second set of candidate configuration values 212-2 is associated with the second set of content items 232-2, the second set of entities 242-2 and the second set of intents 252-2. As yet another example, the third set of candidate configuration values 212-3 is associated with the third set of content items 232-3, the third set of entities 242-3 and the third set of intents 252-3. As another example, the nth set of candidate configuration values 212-n is associated with the nth set of content items to 232-n, the nth set of entities 242-n and the nth set of intents 252-n.

In various implementations, when the configuration parameters 210 are set to a particular set of candidate configuration values, the virtual agent 200 is configured to provide responses to queries based on information provided by the corresponding set of content items. For example, if the configuration parameters 210 are set to the first set of candidate configuration values 212-1, the virtual agent 200 is configured to generate responses to queries based on information provided by the first set of content items 232-1. As such, setting the configuration parameters 210 to a particular set of configuration values results in the virtual agent being transformed into a domain-specific virtual agent. For example, if the second domain corresponds to atorvastatin and the configuration parameters 210 are set to the second set of candidate configuration values 212-2, the virtual agent 200 is transformed into an atorvastatin-specific virtual agent.

Setting the configuration parameters 210 to a particular set of configuration values configures the virtual agent 200 to identify entities and determine an intent of a query based on the set of entities and the set of intents associated with the candidate configuration values that the configuration parameters 210 have been set to. For example, if the configuration parameters 210 are set to the first set of candidate configuration values 212-1, the virtual agent 200 performs entity tagging using the first set of entities 242-1 and determines an intent of the query based on the first set of intents 252-1.

Advantageously, the user 40 may not have to provide a query with a high degree of specificity. For example, the query may not need to indicate the domain to which the query relates. Reducing the need to provide a query with a high degree of specificity may reduce the need for excessively long queries thereby enhancing the user experience of the device 20. For example, if the virtual agent 200 is set to provide responses to queries that relate to the atorvastatin, a user may simply say "side effects" instead of saying "side effects of the atorvastatin". By reducing an amount of effort that the user 40 has to expend, the virtual agent 200 improves the user experience of the device 20. Reducing a length of a query tends to reduce an amount of computing resources associated with interpreting the query.

Figure 1B:
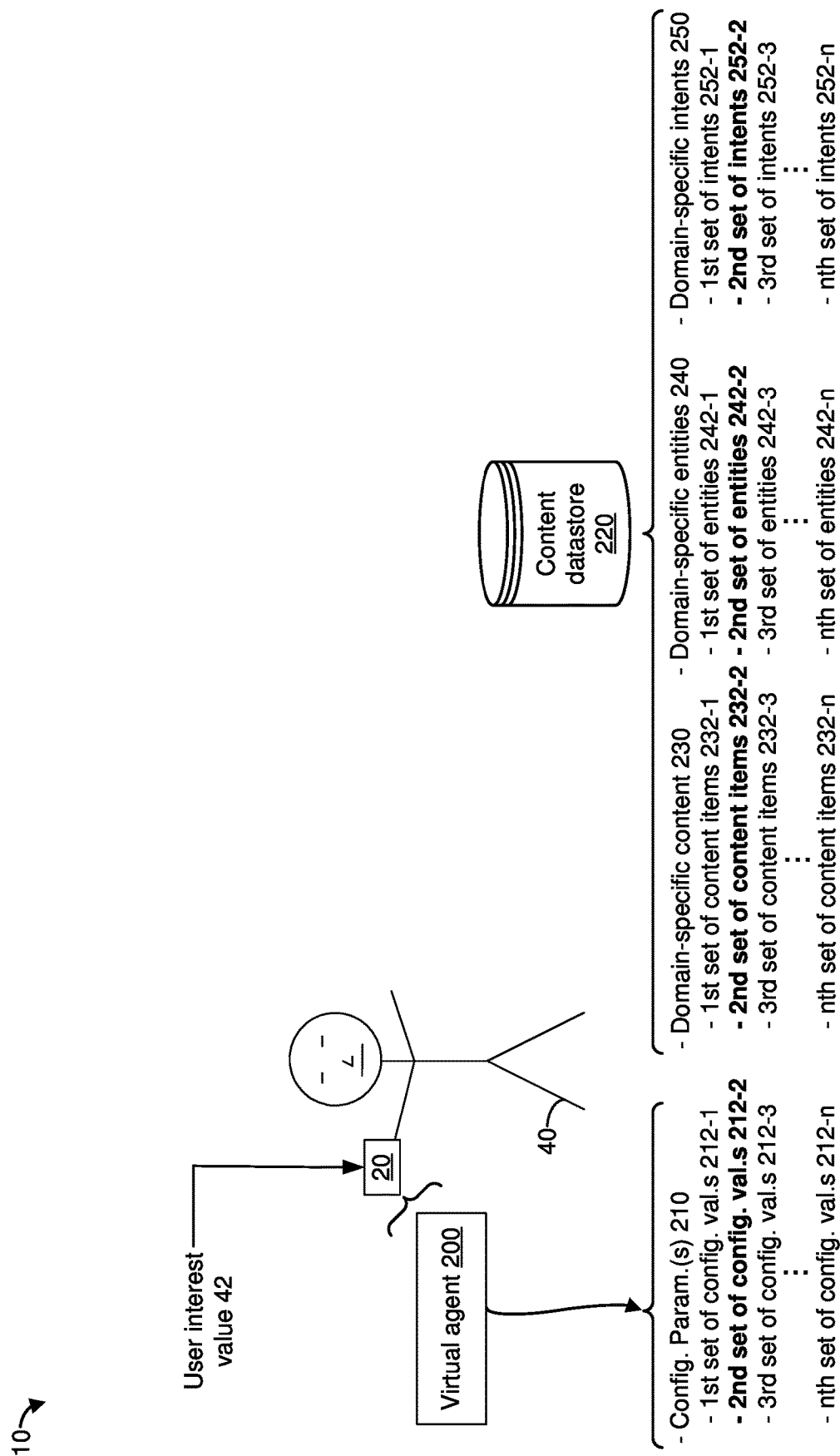

Referring to FIG. 1B, in some implementations, the device 20 determines a user interest value 42 that indicates a domain that the user 40 is interested in learning about. As an example, the user interest value 42 may indicate that the user 40 is interested in learning about a cholesterol-reducing drug (e.g., atorvastatin). As such, the virtual agent 200 sets the configuration parameters 210 to the second set of candidate configuration values 212-2 that are associated with the cholesterol-reducing drug. After the configuration parameters 210 have been set to the second set of candidate configuration values 212-2, the virtual agent 200 provides responses to queries based on the information provided by the second set of content items 232-2 that provides information regarding the cholesterol-reducing drug. As such, while the configuration parameters 210 are set to the second set of candidate configuration values 212-2, the virtual agent 200 operates as an atorvastatin-specific virtual agent that provides responses to queries that relate to the cholesterol-reducing drug.

Figure 1C:
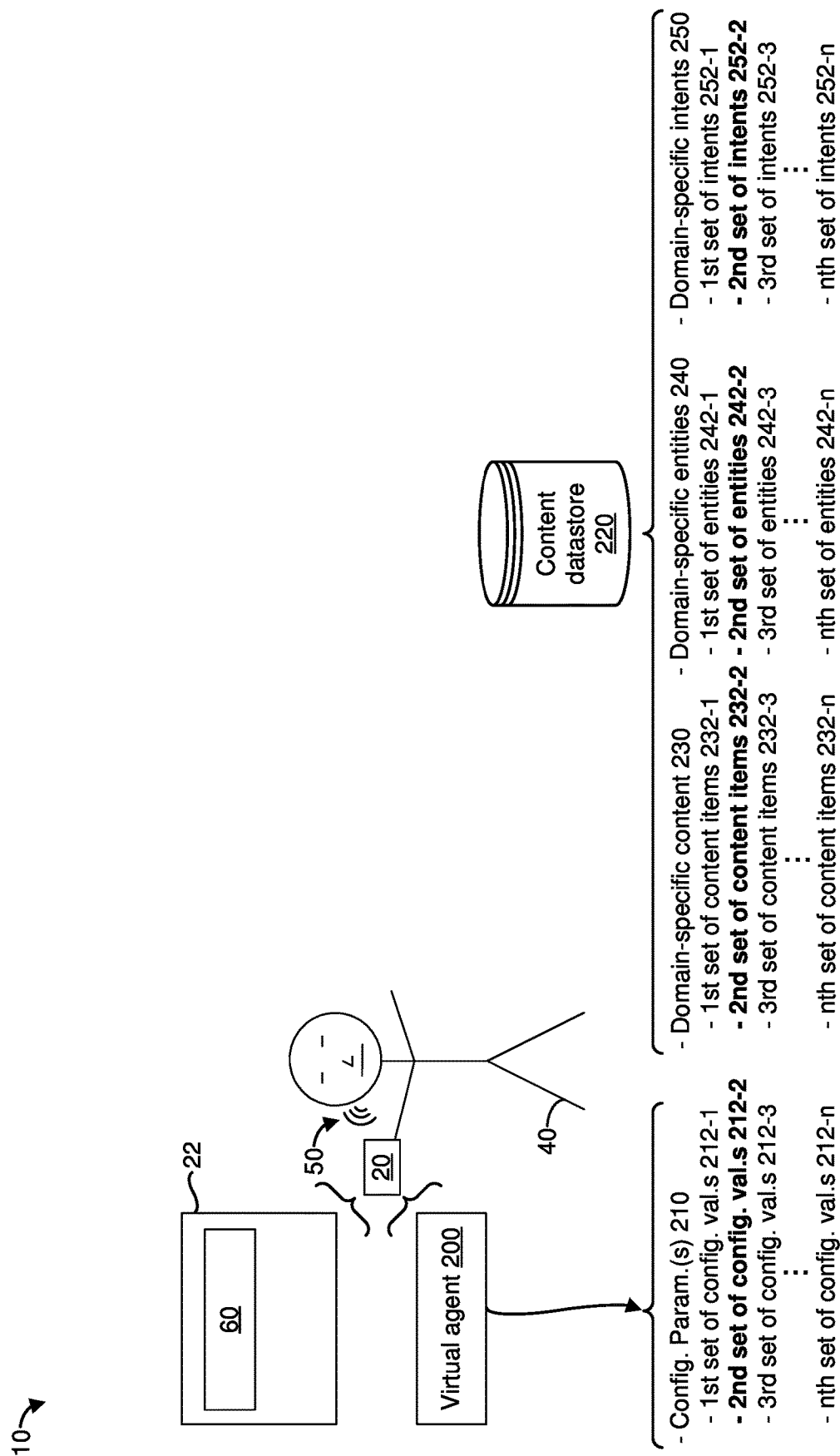

Referring to FIG. 1C, the device 20 receives a query 50 in the form of a voice query that corresponds to an utterance uttered by the user 40. In response to receiving the query 50, the virtual agent 200 generates a response 60 that is displayed on a display 22 of the device 20. When the virtual agent 200 receives the query 50, the virtual agent 200 identifies entities referred to in the query 50 by comparing terms of the query 50 with the second set of entities 242-2. Furthermore, the virtual agent 200 determines an intent associated with the query 50 by comparing the terms of the query 50 with the second set of intents 252-2. Since the virtual agent 200 does not have to compare the terms of the query 50 with the entirety of domain-specific entities 240, the virtual agent 200 uses fewer computing resources to identify entities referenced by the query 50 thereby enhancing operability of the device 20. Similarly, since the virtual agent 200 does not have to compare terms of the query 50 with the entirety of the domain-specific intents 250, the virtual agent 200 uses fewer computing resources to identify the intent associated with the query 50 thereby enhancing operability of the device 20 (e.g., by reducing power consumption by the device 20).

Figure 1D:
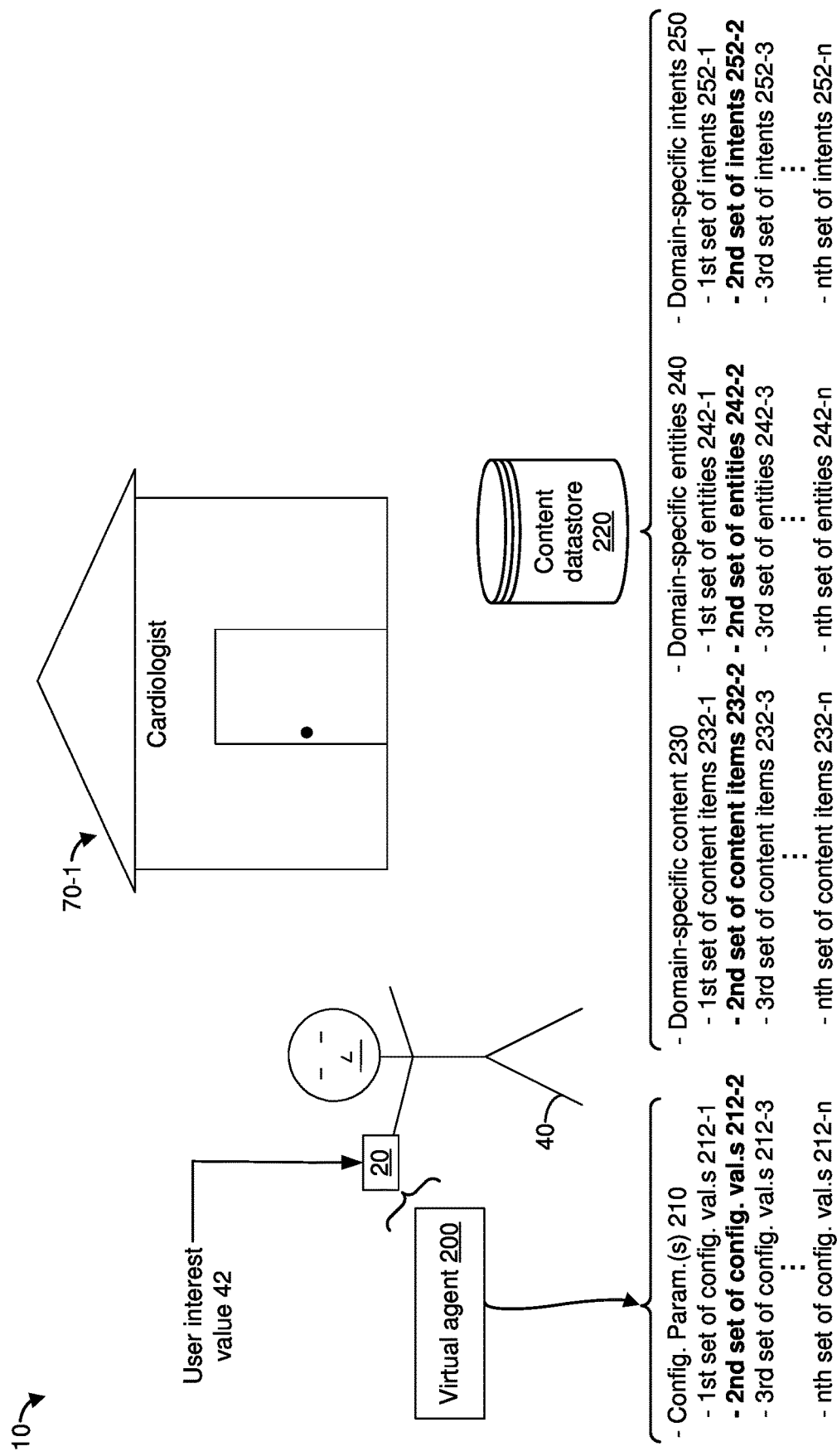
Figure 1E:
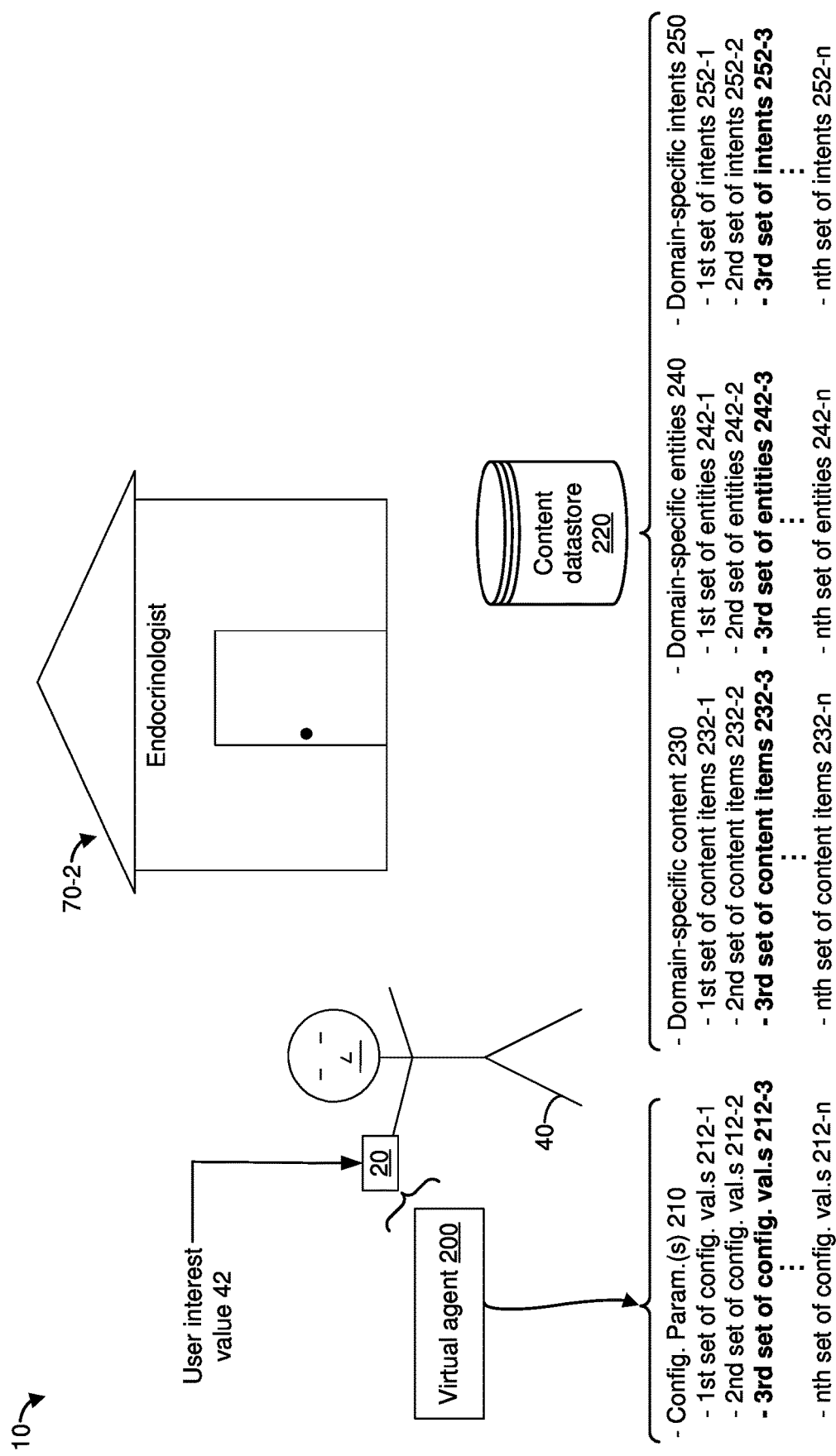

FIGS. 1D and 1E illustrate that, in some implementations, the device 20 determines the user interest value 42 based on a location of the device 20. In the example of FIG. 1D, the device 20 is proximate to (e.g., within a threshold distance of) a first location 70-1 that corresponds to a cardiologist's office. Since the device 20 is at or near the cardiologist's office, the device 20 determines that the user 40 is likely interested in learning about pharmaceutical drugs that treat or prevent cardiac conditions. For example, the device 20 determines that the user 40 is interested in learning about a cholesterol-reducing drug that the user is responsible for discussing with health care providers. As such, in the example of FIG. 1D, the device 20 automatically sets the user interest value 42 to the second domain that corresponds to the cholesterol-reducing drug atorvastatin.

In the example of FIG. 1E, the device 20 is at or proximate to (e.g., within a threshold distance of) a second location 70-2 that corresponds to an endocrinologist's office. As such, the device 20 determines that the user 40 is likely interested in learning about pharmaceutical drugs that treat or ameliorate endocrine conditions. For example, the device 20 determines that the user 40 is likely interested in learning about the blood glucose reducing drug dapagluflozin that the user 40 is responsible for discussing with healthcare providers. As such, in the example of FIG. 1E, the device 20 automatically sets the user interest value 42 to the blood glucose reducing drug dapagluflozin.

By determining the user interest value 42 based on the location of the device 20, the device 20 reduces the need for the user 40 to specify the user interest value 42 either separately or as part of a query that the user 40 provides to the device 20. Reducing the need to manually provide the user interest value 42 tends to reduce a number of user inputs that the user 40 has to provide thereby improving the user experience of the device 20. Reducing the number of user inputs may enhance operability of the device 20 by extending the battery life of the device 20, for example, because the device 20 need not keep the display 22 on while the user 40 is providing the additional user inputs.

Figure 1F:
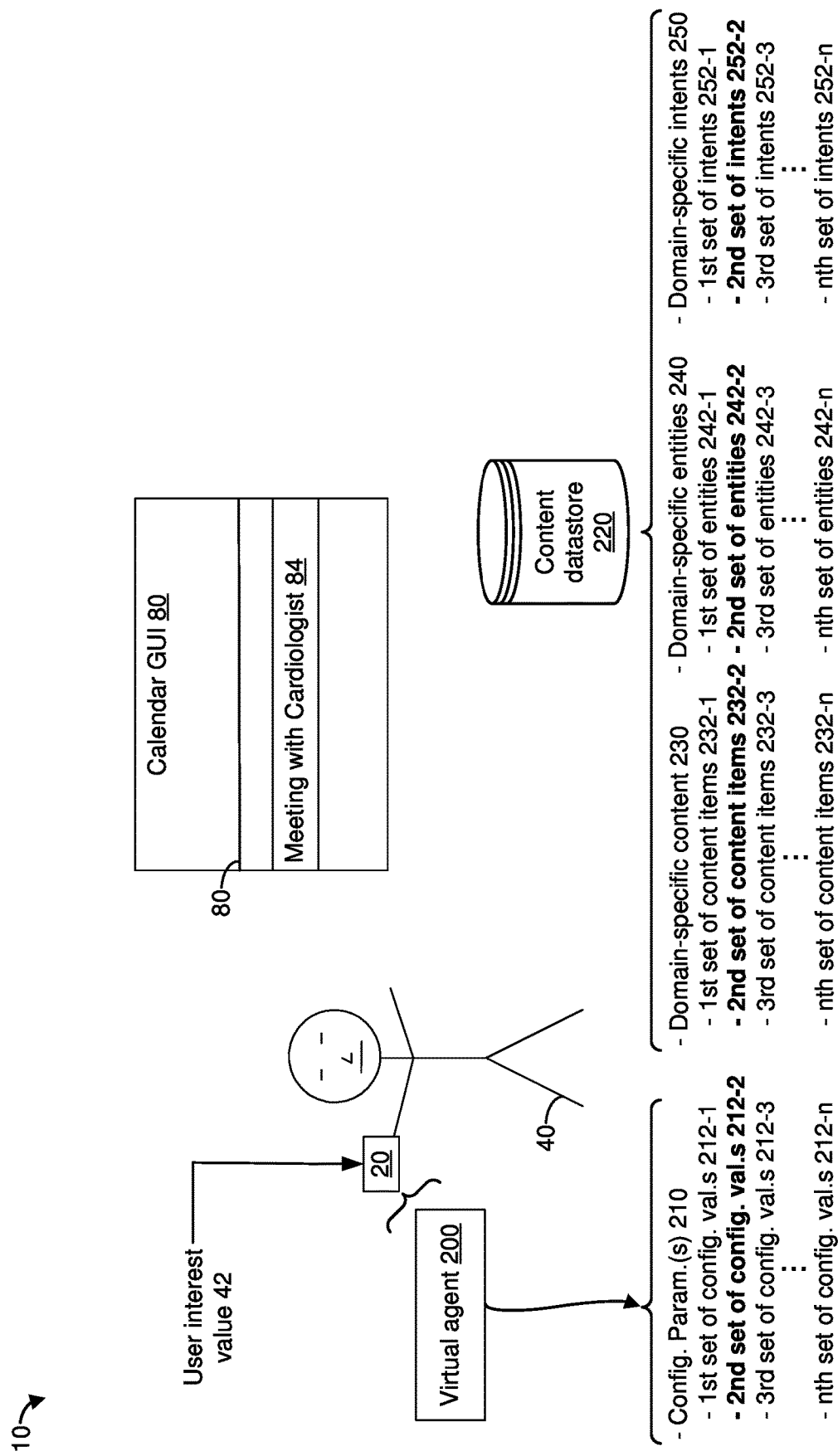
Figure 1G:
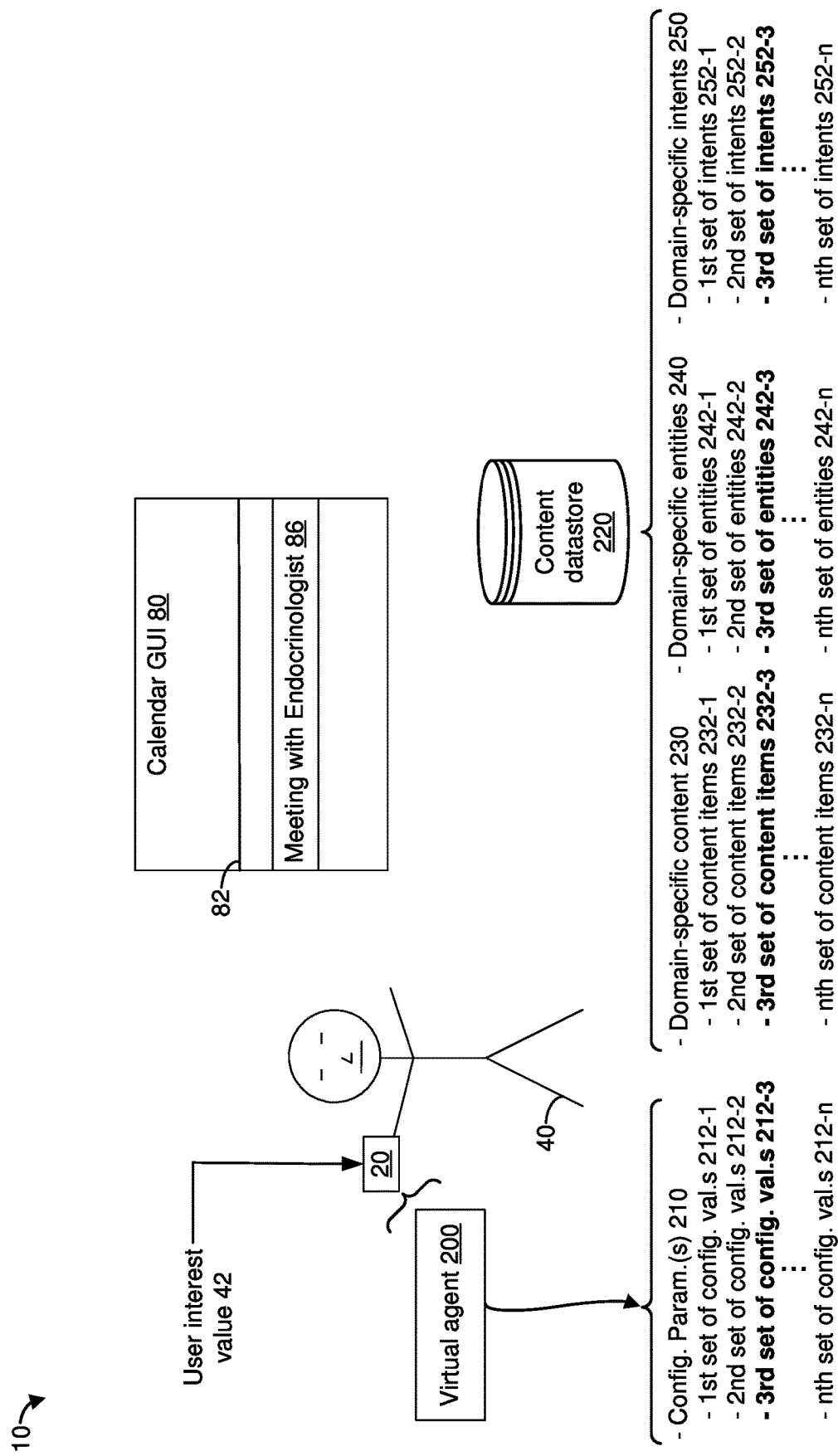

FIGS. 1F and 1G illustrate that, in some implementations, the device 20 determines the user interest value 42 based on calendar data. For example, in some implementations the device 20 includes a calendar application that stores information regarding calendar events. In the example of FIG. 1F, the device 20 includes a calendar application with a calendar graphical user interface (GUI) 80 that displays a current time indicator 82 and a first event indicator 84 that corresponds to a meeting with a cardiologist.

In the example of FIG. 1F, the device 20 automatically sets the user interest value 42 to the cholesterol-reducing drug based on the upcoming event with the cardiologist. Since the user 40 is scheduled to meet with the cardiologist, the device 20 determines that the user 40 is likely interested in learning about or reviewing information regarding the cholesterol-reducing drug that the user 40 may discuss with the cardiologist. As such, configuring the virtual agent 200 to provide information regarding the cholesterol-reducing drug may reduce the amount of time that the virtual agent 200 takes to generate responses to queries that the user 40 provides from a current time to the end of the event.

In the example of FIG. 1G, the calendar GUI 80 includes a second event indicator 86 that corresponds to a meeting with an endocrinologist in the near future. As such, the device 20 automatically sets the user interest value 42 to the blood glucose reducing drug that the user 40 may discuss with the endocrinologist during the upcoming meeting with the endocrinologist. The device 20 automatically configures the virtual agent 200 to provide information regarding the blood glucose reducing drug. As such, from the current time to at least until the end of the event with the endocrinologist, the virtual agent 200 is configured to provide responses to queries based on information provided by the third set of content items 232-3 that is related to the blood glucose reducing drug.

Figure 1H:
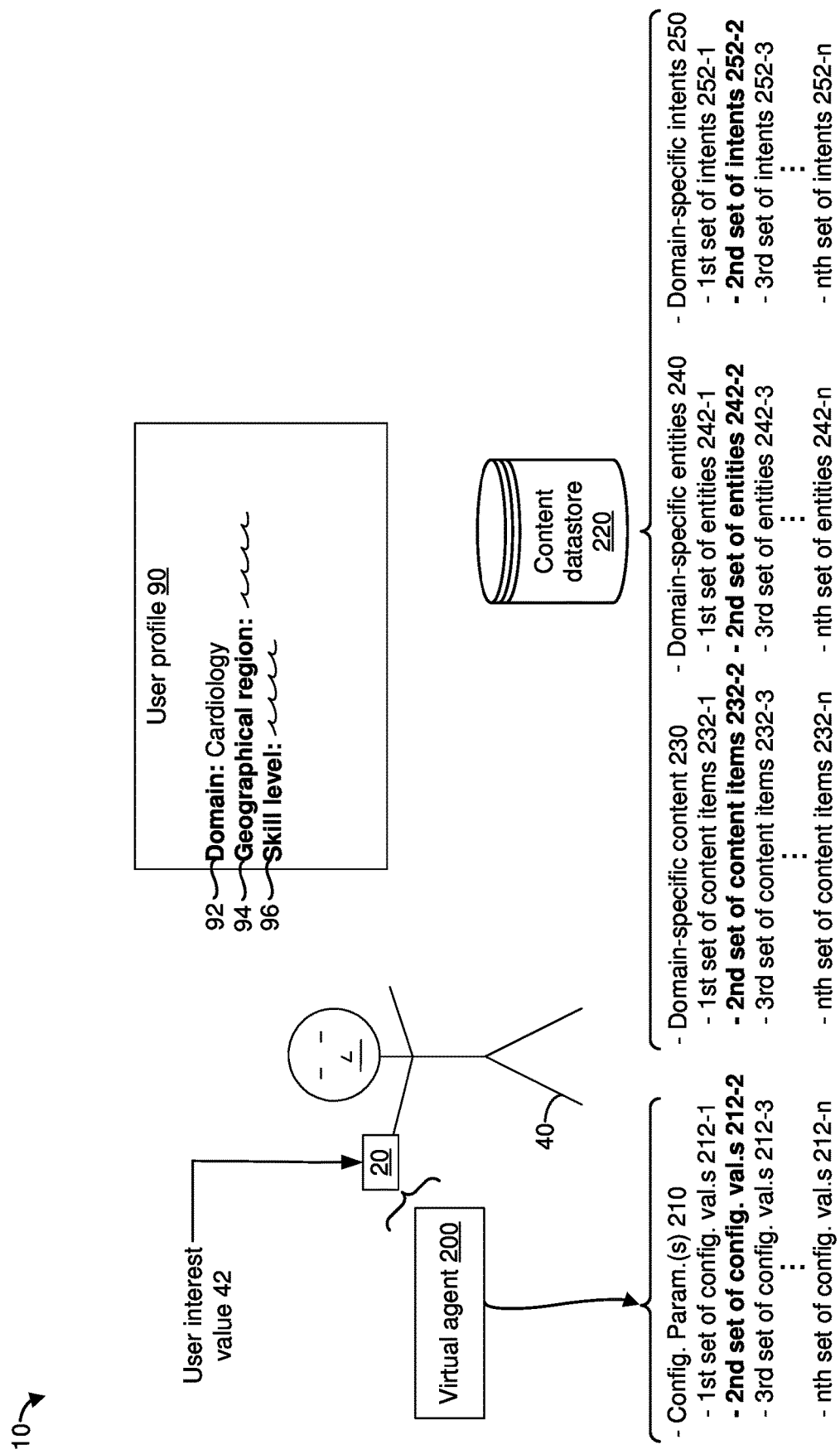
Figure 1I:
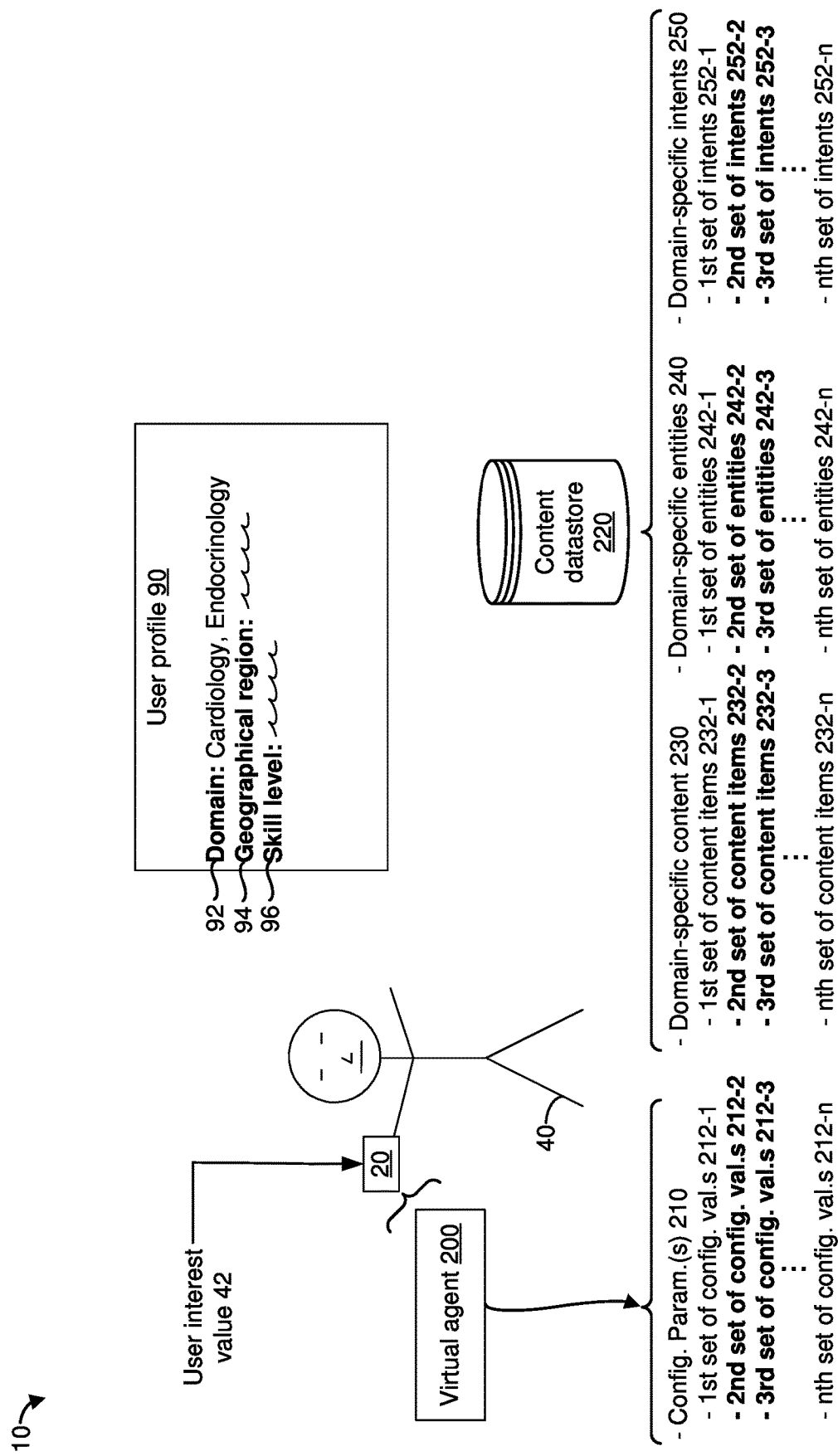

FIGS. 1H and 1I illustrate that, in some implementations, the device 20 configures the virtual agent 200 to operate as a domain-specific virtual agent based on user profile data. FIG. 1H illustrates a user profile 90 that specifies a domain 92 associated with the user profile 90, a geographical region 94 associated with the user profile 90 (e.g., a geographical region where the user 40 works and/or lives, for example, a country, a state, a province, a city and/or a zip code) and a skill level 96 (e.g., a competency level) associated with the user profile 90 (e.g., a skill level of the user 40). In some implementations, the domain 92 refers to one or more pharmaceutical articles that the user 40 is responsible for discussing with healthcare providers. In some implementations, the geographical region 94 indicates a geographic region in which the user 40 is responsible for discussing the pharmaceutical articles with healthcare providers (e.g., physicians, nurse practitioners, physician assistants, etc.). The geographical region 94 may include a region of a continent or a country, a state or a province, a city, and/or a zip code or a postal code. The skill level 96 may indicate the users comprehension level as it relates to the domain 92. In various implementations, the device 20 selects values for the set of configuration parameters 210 based on the domain 92, the geographical region 94, and/or the skill level 96 indicated by the user profile 90. In the example FIG. 1H, the device 20 selects the second set of candidate configuration values 212-2 for the configuration parameters 210 because the domain 92 indicates that the user 40 is responsible for pharmaceutical drugs and medical devices related to cardiology.

Referring to FIG. 1I, the domain 92 indicates that the user 40 is responsible for pharmaceutical articles (e.g., pharmaceutical drugs and medical devices) related to cardiology and endocrinology. As such, the device 20 configures the virtual agent 200 to provide responses that relate to multiple domains. In the example of FIG. 1I, the device 20 sets values of the configuration parameters 210 to the second set of candidate configuration values 212-2 and the third set of candidate configuration values 212-3, so that the virtual agent 200 provides responses that are generated based on the second set of content items 232-2 and the third set of content items 232-3. In the example of FIG. 1I, the user 40 may have to specify in the query which drug the user wants the information about (e.g., in order to allow the device 20 to disambiguate the query and determine whether the user 40 is interested in learning about a cardiac drug or an endocrine drug).

Figure 2:
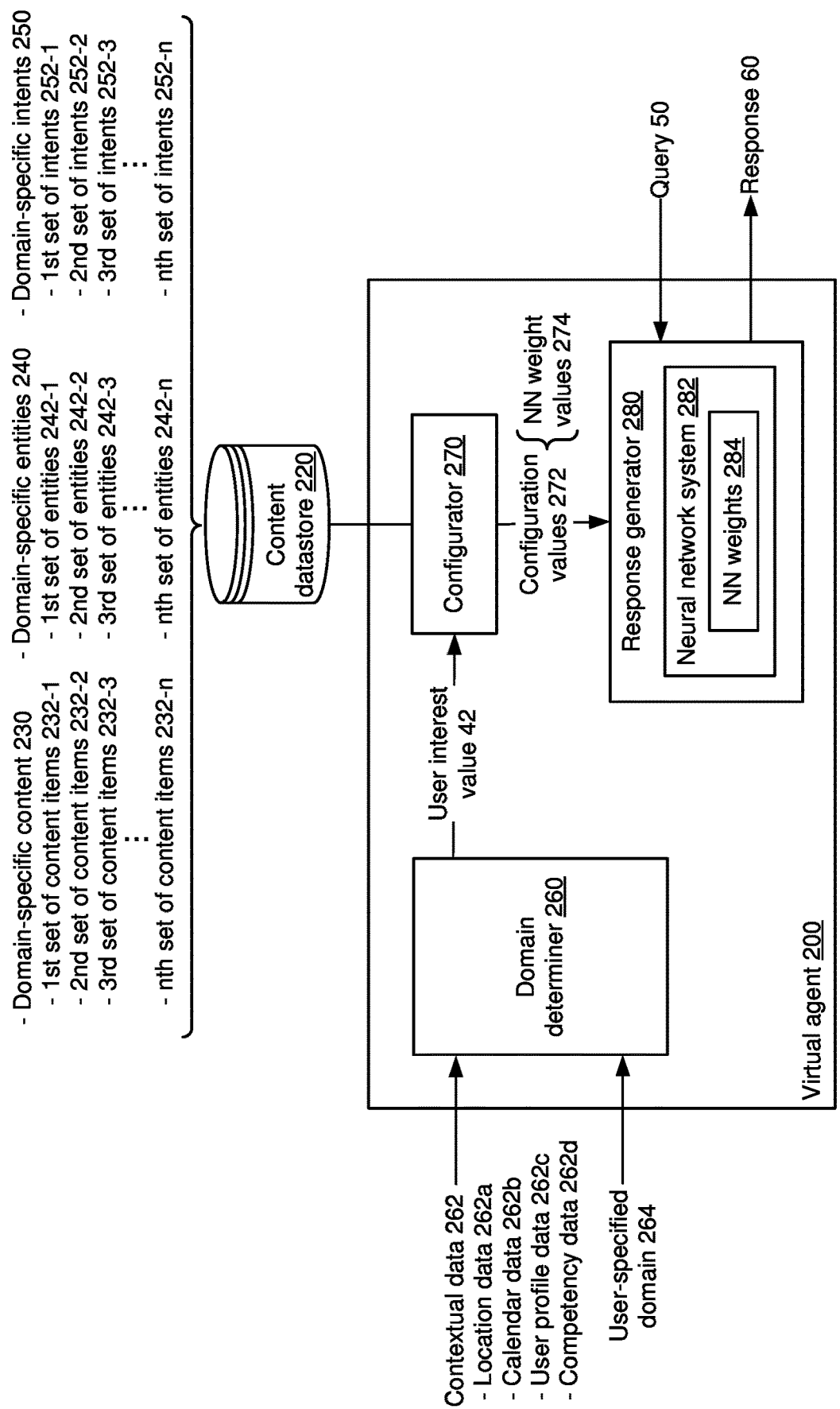
FIG. 2 is a block diagram of a virtual agent in accordance with some implementations.

Referring to FIG. 2, in some implementations, the virtual agent 200 includes a domain determiner 260, a configurator 270 and a response generator 280. In various implementations, the domain determiner 260 determines a domain that a user is interested in learning about, and the configurator 270 configures the response generator 280 based on the domain that the user is interested in learning about. In some implementations, the configurator 270 configures the response generator 280 so as to transform the virtual agent 200 into a domain-specific virtual agent that is limited to generating responses related to the domain that the user is interested in learning about.

In various implementations, the domain determiner 260 determines the user interest value 42 based on contextual data 262 or a user-specified domain 264. In some implementations, the contextual data 262 includes location data 262a that indicates a location of a device (e.g., the device 20 shown in FIGS. 1A-1I) or a user (e.g., the user 40 shown in FIGS. 1A-1I) that the virtual agent 200 is serving. In some implementations, the domain determiner 260 determines the user interest value 42 based on the location data 262a. For example, certain locations may be associated with particular domains and the domain determiner 216 determines whether the location data 262a indicates that a current location of the device matches a particular location associated with a particular domain. As an example, referring to FIG. 1D, the domain determiner 260 sets the configuration parameters 210 to the second set of candidate configuration values 212-2 in response to the location data 262a indicating that the device 20 is within a threshold distance of a type of location associated with the second set of candidate configuration values 212-2 (e.g., in response to the location data 262a indicating that the device 20 is within a threshold distance of a cardiologist's office). As another example, referring to FIG. 1E, the domain determiner 260 sets the configuration parameters 210 to the third set of candidate configuration values 212-3 in response to the location data 262a indicating that the device 20 is within a threshold distance of a type of location associated with the third set of candidate configuration values 212-3 (e.g., in response to the location data 262a indicating that the device 20 is within a threshold distance of an endocrinologist's office).

In some implementations, the domain determiner 260 determines the user interest value 42 based on calendar data 262b that includes information regarding calendar events stored in a calendar application. For example, in some implementations, the calendar data 262b indicates that a current event or an upcoming event relates to a particular domain. In such implementations, the domain determiner 260 determines that the user is likely interested in learning about the domain related to the current event or the upcoming event. As such, the domain determiner 260 sets the user interest value 42 to the domain related to the current event or the upcoming event. As an example, referring to FIG. 1F, the domain determiner 260 sets the configuration parameters 210 to the second set of candidate configuration values 212-2 in response to the calendar data 262b indicating an upcoming event with a cardiologist. As another example, referring to FIG. 1G, the domain determiner 260 sets the configuration parameters 210 to the third set of candidate configuration values 212-3 in response to the calendar data 262b indicating an upcoming event with an endocrinologist. In some implementations, when the domain determiner 260 determines the user interest value 42 based on the calendar data 262b, the domain determiner 260 associates an expiration time with the user interest value 42. In some implementations, the expiration time is a function of a start time and/or an end time of a calendar event indicated by the calendar data 262b. For example, in some implementations, the user interest value 42 expires (e.g., resets to a default value) when the event ends.

In some implementations, the domain determiner 260 determines the user interest value 42 based on user profile data 252c that indicates a user profile associated with a user (e.g., the user profile 90 shown in FIGS. 1H and 1I). In some implementations, the user profile data 252c specifies a set of one or more domains (e.g., a set of one or more pharmaceutical articles) that the user is interested in learning about or a set of one or more domains that the user is responsible for learning about (e.g., as part of a training plan or a lesson plan). In some implementation, the domain determiner 260 sets the user interest value 42 to a domain indicated by the user profile data 262c. As an example, referring to FIG. 1H, the domain determiner 260 sets the configuration parameters 210 to the second set of candidate configuration values 212-2 in response to the domain 92 in the user profile 90 being cardiology. As another example, referring to FIG. 1I, the domain determiner 260 sets the configuration parameters 210 to the second set of candidate configuration values 212-2 and the third set of candidate configuration values 212-3 in response to the domain 92 in the user profile 90 being cardiology and endocrinology.

In some implementations, the domain determiner 260 determines the user interest value 42 based on competency data 262d that indicates a competency level (e.g., a skill level, for example, a comprehension level) of a user. In some implementations, the competency data 262d indicates a competency level (e.g., a skill level and/or a comprehension level) of the user in a particular domain. In some implementations, the domain determiner 260 sets the user interest value 42 to the particular domain in response to the competency data 262d indicating that the competency level of the user breaches (e.g., is below) a competency threshold. In some implementations, the competency data 262d indicates that an amount of knowledge possessed by the user in relation to a particular domain is less than a threshold amount of knowledge. In such implementations, the domain determiner 260 sets the user interest value 42 to that particular domain so that the user can learn more about that particular domain and improve the user's competency level with respect to that particular domain.

In some implementations, the domain determiner 260 receives an input (e.g., a user input, for example, a voice input) that specifies a user-specified domain 264. In some implementations, the domain determiner 260 sets the user interest value 42 to the user-specified domain 264. For example, in some implementations, the user specifies that the user is interested in learning about a particular domain, and the domain determiner 260 sets the user interest value 42 to the domain indicated by the user via the user input.

In various implementations, the configurator 270 configures the response generator 280 based on the user interest value 42. In some implementations, the response generator 280 includes a neural network system 282 that includes a set of one or more neural networks. In some implementations, the neural network system 282 is associated with a set of one or more neural network weights 284. In various implementations, the configurator 270 determines configuration values 272 for the response generator 280. In some implementations, the configuration values 272 include neural network weight values 274 for the neural network weights 284. In some implementations, the configurator 270 determines the configuration values 272 by selecting a set of candidate configuration values that are associated with a domain (e.g., a pharmaceutical article) referenced by the user interest value 42. For example, in some implementations, the configurator 270 determines the configuration values 272 by selecting one of the sets of candidate configuration values 212-1, 212-2, 212-3, ..., and 212-n shown in FIGS. 1A-1I. In some implementations, the configurator 270 retrieves the configuration values 272 from the content datastore 220.

In various implementations, by setting the configuration values 272 for the response generator 280 based on the user interest value 42, the configurator 270 configures the virtual agent 200 to generate the response 60 to the query 50 based on a set of content items that provide information regarding the domain indicated by the user interest value 42. As such, after the configurator 270 provides the configuration values 272 to the response generator 280, the response generator 280 is limited to generating responses to queries based on information provided by a set of content items that relate to the domain indicated by the user interest value 42. In some implementations, after the configurator 270 configures the response generator 280 with the configuration values 272, the response generator 280 is limited to perform entity tagging in the query 50 by comparing terms of the query 50 with a set of entities that are associated with the domain indicated by the user interest value 42 (e.g., instead of comparing terms of the query 50 with entities that are associated with other domains). In some implementations, configuring the response generator 280 with the configuration values 272 reduces utilization of computing resources associated with entity tagging. In some implementations, after the configurator 270 configures the response generator 280 with the configuration values 272, the response generator 280 is limited to determining an intent of the query 50 by comparing terms of the query 50 with a set of intents that are associated with the domain indicated by the user interest value 42 (e.g., instead of comparing terms of the query 50 with intents that are associated with other domains). In some implementations, configuring the response generator 280 with the configuration values 272 reduces utilization of computing resources associated with determining the intent.

Figure 3:
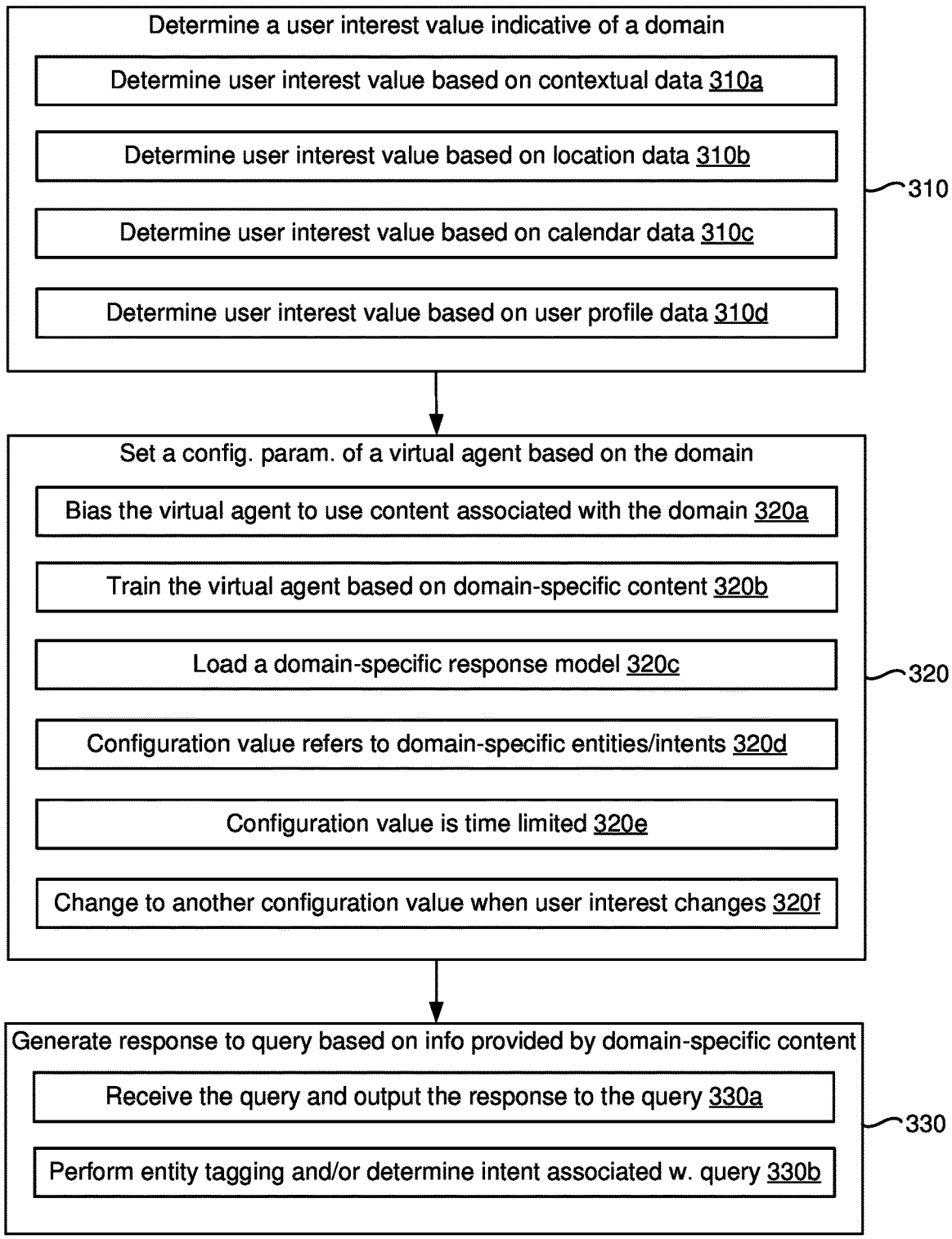
FIG. 3 is a flowchart representation of a method of configuring a virtual agent to provide domain-specific responses in accordance with some implementations.

FIG. 3 is a flowchart representation of a method 300 of configuring a virtual agent to provide domain-specific responses. In various implementations, the method 300 is performed by a device including a non-transitory memory and a processor coupled with the non-transitory memory (e.g., the device 20 shown in FIGS. 1A-1I, and/or the virtual agent 200 shown in FIGS. 1A-2). In some implementations, the method 300 is performed by processing logic, including hardware, firmware, software, or a combination thereof. In some implementations, the method 300 is performed by a processor executing code stored in a non-transitory computer-readable medium (e.g., a memory).

As represented by block 310, in various implementations, the method 300 includes determining a user interest value indicative of a pharmaceutical article that the user is interested in learning about. In some implementations, the pharmaceutical article is associated with a set of media content items that provide information regarding the pharmaceutical article. For example, as shown in FIG. 2, the domain determiner 260 determines the user interest value 42 indicative of a domain that the user is interested in learning about. As shown in FIG. 1B, a domain indicated by the user interest value 42 is associated with the second set of content items 232-2 that provide information regarding the domain.

As represented by block 310a, in some implementations, determining the user interest value includes determining the user interest value based on contextual data indicating a context of the device or a user of the device. For example, as shown in FIG. 2, the domain determiner 260 determines the user interest value 42 based on the contextual data 262. Examples of contextual data include location data indicating a location of the device (e.g., the location data 262a shown in FIG. 2), calendar data indicating a calendar event stored in a calendar application (e.g., the calendar data 262b shown in FIG. 2), user profile data associated with the device or the user of the device (e.g., the user profile data 262c shown in FIG. 2), competency data indicating a competency level of the user (e.g., the competency data 262d shown in FIG. 2), and/or a current time. In some implementations, determining the user interest value based on the contextual data reduces the need for a sequence of user inputs corresponding to the user manually specifying the domain that the user is interested in learning about. Reducing unnecessary user inputs conserves computing resources associated with processing (e.g., detecting and/or interpreting) user inputs thereby reducing power consumption of the device and enhancing operability of the device by extending a battery life of the device.

As represented by block 310b, in some implementations, determining the user interest value includes determining the user interest value based on a geographical location of the device (e.g., based on the location data 262a shown in FIG. 2). For example, as shown in FIG. 1D, when the device 20 is near (e.g., within a threshold distance of) a cardiologist's office, the device 20 determines that the user 40 is likely interested in learning about cardiac medications such as a cholesterol-reducing drug. As such, in the example of FIG. 1D, the device 20 sets the user interest value 42 to the cholesterol-reducing drug. As another example, as shown in FIG. 1E, when the device 20 is near (e.g., within a threshold distance of) an endocrinologist's office, the device 20 determines that the user 40 is likely interested in learning about endocrine related medications such as a blood glucose reducing drug or an insulin delivery device (e.g., an insulin pump). As such, in the example of FIG. 1E, the device 20 sets the user interest value 42 to the blood glucose reducing drug.

In some implementations, the pharmaceutical article includes a pharmaceutical drug or a medical device that treats a particular medical condition. In some implementations, determining the user interest value includes obtaining a current geographical location of the device, determining a distance between the current geographical location of the device and a geographical location where a healthcare provider treats the particular medical condition, and setting the user interest value to a value corresponding to the pharmaceutical article in response to the distance being less than a threshold distance.

In some implementations, the pharmaceutical article includes a pharmaceutical drug or a medical device that treats a particular medical condition. In some implementations, determining the user interest value includes obtaining, from a navigation application (e.g., a maps application), a destination location that the navigation application is providing navigational directions to, and setting the user interest value to a value corresponding to the pharmaceutical article in response to determining that the destination location corresponds to a geographical location where a healthcare provider treats the particular medical condition.

As represented by block 310c, in some implementations, determining the user interest value includes determining the user interest value based on a calendar event stored in a calendar application (e.g., based on calendar data 262b shown in FIG. 2). For example, as shown in FIG. 1F, when the calendar application indicates that the user 40 has an upcoming event that corresponds to a meeting with a cardiologist, the device 20 determines that the user is likely interested in learning about cardiac medications (e.g., the cholesterol-reducing drug). As such, in the example of FIG. 1F, the device 20 sets the user interest value 42 to the cholesterol-reducing drug. As another example, as illustrated in FIG. 1G, when the calendar application indicates that the user has an upcoming event that corresponds to a meeting with an endocrinologist, the device 20 determines that the user 40 is likely interested in learning about the blood glucose reducing drug. As such, in the example of FIG. 1G, the device 20 sets the user interest value 42 to the blood glucose reducing drug.

In some implementations, the pharmaceutical article includes a pharmaceutical drug or a medical device that treats a particular medical condition. In some implementations, determining the user interest value includes obtaining calendar data indicative of a future calendar event that is scheduled at a time that is within a threshold time duration of a current time, and setting the user interest value to a value corresponding to the pharmaceutical article in response to determining that the future calendar event corresponds to a meeting with a healthcare provider that treats the particular medical condition.

As represented by block 310d, in some implementations, determining the user interest value includes determining the user interest value based on a user profile (e.g., based on user profile data 262c shown in FIG. 2). In some implementations, the user profile indicates a set of one or more domains that are associated with the user. For example, as shown in FIG. 1H, the user profile 90 indicates that a domain 92 associated with the user is cardiology indicative of the user's responsibility to learn information about cardiac drugs. As such, in the example of FIG. 1H, the device 20 sets the user interest value 42 to the cholesterol-reducing drug. As another example, as shown in FIG. 1I, the user profile 90 indicates that a domain 92 associated with the user is cardiology and endocrinology indicative of the user's responsibility to learn information about cardiac drugs and endocrine drugs. As such, in the example of FIG. 1I, the device 20 sets the user interest value 42 to the cholesterol-reducing drug and the blood glucose reducing drug.

In some implementations, determining the user interest value includes obtaining user profile data indicative of a set of one or more pharmaceutical articles that a user of the device is responsible for discussing with healthcare providers, and setting the user interest value to a value corresponding to the pharmaceutical article in response to the set of one or more pharmaceutical articles including the pharmaceutical article.

In some implementations, determining the user interest value includes obtaining user profile data indicative of a plurality of pharmaceutical articles that a user of the device is responsible for discussing with healthcare providers. In some implementations, the method 300 includes determining respective user comprehension scores for the plurality of pharmaceutical articles. In some implementations, the respective user comprehension scores indicate corresponding user comprehension levels of the user with regards to information related to the plurality of pharmaceutical articles. In some implementations, the method 300 includes setting the user interest value to a value corresponding to the pharmaceutical article in response to the pharmaceutical article being associated with a lowest one of the respective user comprehension scores.

As represented by block 320, in some implementations, the method 300 includes setting a configuration parameter of the virtual agent to a configuration value that is based on the pharmaceutical article indicated by the user interest value. For example, as shown in FIG. 2, the configurator 270 sets the configuration parameters of the virtual agent 200 to the configuration values 272 that are based on the domain indicated by the user interest value 42. In various implementations, setting the configuration parameter of the virtual agent to a configuration value that is based on the user interest value configures the virtual agent to operate as a domain-specific virtual agent that is limited to generating responses based on information associated with the domain indicated by the user interest value. In some implementations, configuring the virtual agent to operate as a domain-specific virtual agent increases a relevance of the responses that the virtual agent generates thereby enhancing operability of the device. In some implementations, setting the configuration parameter based on the user interest value decreases an amount of resources (e.g., computing resources and/or time) associated with generating responses to queries related to the domain indicated by the user interest value thereby enhancing operability of the device, for example, by reducing power consumption of the device.

As represented by block 320a, in some implementations, setting the configuration parameter of the virtual agent to the configuration value includes biasing the virtual agent to use the set of content items associated with the pharmaceutical article to generate responses to queries while the configuration parameter is set to the configuration value that is based on the pharmaceutical article indicated by the user interest value. For example, as shown in FIG. 1B, setting the configuration parameters 210 to the second set of candidate configuration values 212-2 biases the virtual agent 200 so that the virtual agent 200 is more likely to generate responses or queries based on information provided by the second set of content items 232-2 than the other sets of content items 232-1, 232-3, . . . , and 232-n. In some implementations, biasing the virtual agent to use the set of media content items associated with a domain causes the virtual agent to assign a greater weight to the set of media content items associated with the domain and a lower weight to media content items that are not associated with the domain.

In some implementations, biasing the virtual agent to use the set of content items associated with the domain (e.g., the pharmaceutical article) indicated by the user interest value includes tagging entities in the query that match entities extracted from the set of media content items associated with the domain, and foregoing tagging of entities in the query that were extracted from content items that are not associated with the domain. In some implementations, biasing the virtual agent includes identifying an intent associated with the query based on a set of intents extracted from or associated with the set of media content items related to the domain, and not based on intents that are associated with media content items that are not related to the domain. In some implementations, biasing the virtual agent to use a set of media content items associated with domain causes the virtual agent to generate responses to queries in a shorter amount of time thereby conserving computing cycles.

As represented by block 320b, in some implementations, setting the configuration parameter of the virtual agent to the configuration value includes utilizing the set of media content items associated with the pharmaceutical article to train the virtual agent. As an example, in FIG. 1B, the device 20 may train the virtual agent 200 using the second set of content items 232-2 so that the virtual agent 200 generates responses based on information provided by the second set of content items 232-2. Training the virtual agent to generate responses based on information provided by the media content items related to the domain tends to reduce the amount of time associated with generating responses. Training the virtual agent using the media content items related to the domain tends to make the responses more relevant to the domain thereby enhancing operability of the device.

As represented by block 320c, in some implementations, setting the configuration parameter of the virtual agent to the configuration value includes loading a response generation model (hereafter "model") that has been trained using the set of media content items associated with the pharmaceutical article. In some implementations, loading the model includes selecting the model from a variety of models that have been trained using respective sets of media content items associated with corresponding domains. For example, referring to FIG. 1D, the content datastore 220 may store a plurality of models that have been trained using respective ones of the sets of content items. For example, the content datastore 220 may store a first model that has been trained using the first set of content items 232-1, a second model that has been trained using the second set of content items 232-2, a third model that has been trained using the third set of content items 232-3, . . . , and an nth model that has been trained using the nth set of content items 232-n. In some implementations, each model has been trained such that the model provides responses to queries based on information provided by the content items that were used to train the model. For example, the first model provides responses based on information provided by the first set of content items 232-1. Similarly, the second model generates responses to queries based on information provided by the second set of content items 232-2. Loading a domain-specific model allows the virtual agent to generate responses that are more relevant to the domain that the user is interested in learning about thereby increasing operability of the device and/or enhancing the user experience of the device.

As represented by block 320d, in some implementations, the configuration value refers to a set of entities that are extracted from the set of media content items associated with the pharmaceutical article. For example, as shown in FIG. 1B, the second set of candidate configuration values 212-2 references the second set of entities 242-2 that are extracted from the second set of content items 232-2. In some implementations, the configuration value specifies a domain-specific vocabulary (e.g., domain-specific glossary or a domain-specific dictionary) that is used to tag entities in the query, and to determine the intent associated with the query. In some implementations, the configuration value refers to a set of intents that are associated with the domain. For example, as shown in FIG. 1B, the second set of candidate configuration values 212-2 may refer to the second set of intents 252-2 that are associated with the second domain.

As described herein, the second set of intents 252-2 may have been extracted from the second set of content items 232-2 and/or the second set of intents 252-2 may have been provided by an operator, for example, a human operator. Associating a set of domain-specific entities with the virtual agent allows the virtual agent to identify entities in the query. Specifically, associating domain-specific entities with the virtual agent allows the virtual agent to identify entities that tend to be more relevant to the domain that the user is interested in learning about. In some implementations, foregoing association of the virtual agent with entities that are extracted from content items related to other domains tends to improve the likelihood that entities identified in the query are relevant to the domain.

As represented by block 320e, in some implementations, setting the configuration parameter includes setting the configuration parameter to the configuration value for a particular amount of time. In some implementations, after that particular amount of time expires the configuration parameter is reset to a default configuration value. As such, in some implementations, the virtual agent is transformed into a domain-specific virtual agent for a particular amount of time and the virtual agent reverts to a generic virtual agent (e.g., a domain-agnostic virtual agent) after that particular amount of time expires.

In some implementations, the method 300 includes setting the configuration parameter to the configuration value for a time duration of a calendar event that is related to the pharmaceutical article. For example, the configuration parameter may be set to the configuration value during the calendar event and/or for a predetermined amount of time prior to the calendar event. For example, as shown in FIG. 1F, the configuration parameters 210 are set to the second set of candidate configuration values 212-2 that correspond to the cholesterol-reducing drug during the calendar event indicated by the first event indicator 84 and for an amount of time prior to the calendar event. As such, after the meeting corresponding to the calendar event has occurred, the configuration parameters 210 may be reset to a default value. Transforming the virtual agent into a domain-specific virtual agent based on calendar event data tends to improve the user experience of the device by allowing the user to search for information related to the calendar event in a more accessible manner. For example, if the user says "side effects" during or a certain amount of time prior to the calendar event with the endocrinologist, the device automatically determines that the user is interested in learning about the side effects of the blood glucose reducing drug. As such, in this example, the user does not have to say "side effects of the blood glucose reducing drug". As another example, if the user says "side effects" during or a certain amount of time prior to the calendar event with the cardiologist, the device automatically determines that the user is interested in learning about the side effects of the cholesterol-reducing drug. As such, in this example, the user does not have to say "side effects of the cholesterol-reducing drug".

In some implementations, the method 300 includes setting the configuration parameter to the configuration value while a user profile is associated with the pharmaceutical article and resetting the configuration parameter to a default value in response to detecting that the user profile is not associated with the pharmaceutical article (e.g., in response to detecting that the user profile is subsequently dissociated with the pharmaceutical article). For example, as shown in FIG. 1H, the device 20 sets the configuration parameters 210 to the second set of candidate configuration values 212-2 because the domain 92 is associated with cardiology. In the example of FIG. 1H, if the domain 92 is changed to another domain (e.g., endocrinology), the configuration parameters 210 may be changed from the second set of candidate configuration values 212-2 to the third set of candidate configuration values 212-3. Moreover, if the user is no longer associated with the cholesterol-reducing drug (e.g., because the user leaves a company that manufacturers the cholesterol-reducing drug), the user profile may be reset and subsequently the configuration parameter may be reset in response to the user profile being reset. Setting the configuration parameter based on user profile allows the user to learn about domains that are associated with the user profile without having to provide queries with a relatively high degree of specificity (e.g., without having to specify the domain as part of the query). For example, when the user says "side effects", the device automatically determines that the user is interested in learning about the side effects of the cholesterol-reducing drug because the user profile is associated with the cholesterol-reducing drug. As such, in this example, the user does not have to say "side effects of the cholesterol-reducing drug".

As represented by block 320f, in some implementations, the method 300 includes determining a second user interest value indicative of a second pharmaceutical article that the user is interested in learning about, setting (e.g., switching) the configuration parameter to a second configuration value that is based on the second pharmaceutical article, and after setting the configuration parameter to the second configuration value, generating, by the virtual agent, a second response to a second query based on information provided by a second set of media content items associated with the second pharmaceutical article. For example, as shown in FIGS. 1H and 1I, the device 20 changes values of the configuration parameters 210 from the second set of candidate configuration values 212-2 to the second set of candidate configuration values 212-2 and the third set of candidate configuration values 212-3 in response to detecting a change in the domain that the user is interested in learning about. Advantageously, as the device detects a change in the domain that the user is interested in learning about, the device automatically transforms (e.g., repurposes) the virtual agent into another domain-specific virtual agent that is capable of generating responses to queries related to the second domain that the user is interested in learning about.

As represented by block 330, in various implementations, the method 300 includes, after setting the configuration parameter of the virtual agent, generating, by the virtual agent a response to a query based on the information provided by the set of media content items associated with the pharmaceutical article. For example, as shown in FIG. 2, the virtual agent 200 receives a query 50 and generates a response 60 for the query 50. In various implementations, configuring the virtual agent based on the domain that the user is interested in learning about increases a likelihood of the response being more tailored to the domain and thereby being more relevant to the query. In various implementations, configuring the virtual agent based on the domain that the user is interested in learning about tends to reduce an amount of computing resources that the virtual agent uses to generate a response. For example, limiting a number of entities that the virtual agent has to compare the terms of the query with reduces an amount of time that the virtual agent takes to generate the response.

As represented by block 330a, in some implementations, the method 300 includes receiving, by the virtual agent, an input that corresponds to the query. For example, as shown in FIG. 1C, the device 20 receives an audio signal that corresponds to the query 50. In some implementations, the user may input the query into the device (e.g., via a keyboard). In some implementations, the method 300 includes outputting the response to the query. For example, as shown in FIG. 1C, the device 20 displays the response 60 on the display 22. Alternatively or additionally, in some implementations, the method 300 includes playing audio corresponding to the response. For example, the device 20 may output audio, via a speaker of the device, that corresponds to the response 60.

As represented by block 330b, in some implementations, generating the response include performing entity tagging by matching terms in the query with entities that are specific to the pharmaceutical article and are included in a set of entities referenced by the configuration value. For example, as described in relation to FIG. 1C, in some implementations, the virtual agent 200 identifies entities referenced in the query 50 by matching terms of the query with the second set of entities 242-2. Performing entity tagging allows the virtual agent to provide a response to the query by identifying portions of information in the corresponding set of content items that are related to the entity (e.g., by identifying portions of information that are tagged with the entity, or by identifying portions of the information that relate to the entity).

In some implementations, generating the response includes determining an intent associated with the query by matching terms in the query with intents that are specific to the pharmaceutical article and are included in a set of intents referenced by the configuration value, and synthesizing the response in order to satisfy the intent associated with the query. For example, as described in relation to FIG. 1C, in some implementations, the virtual agent 200 determines an intent associated with the query 50 by comparing or matching terms in the query 50 with the second set of intents 252-2. In some implementations, after identifying entities in the query 50 and determining the intent of the query 50, the virtual agent 200 generates the response 60 in order to satisfy the intent. In various implementations, entities and intents are different for different domains. As such, by allowing the configuration value to reference domain-specific entities and domain-specific intents, the virtual agent reduces an amount of time associated with identifying entities in the query and determining an intent associated with the query.

Figure 4:
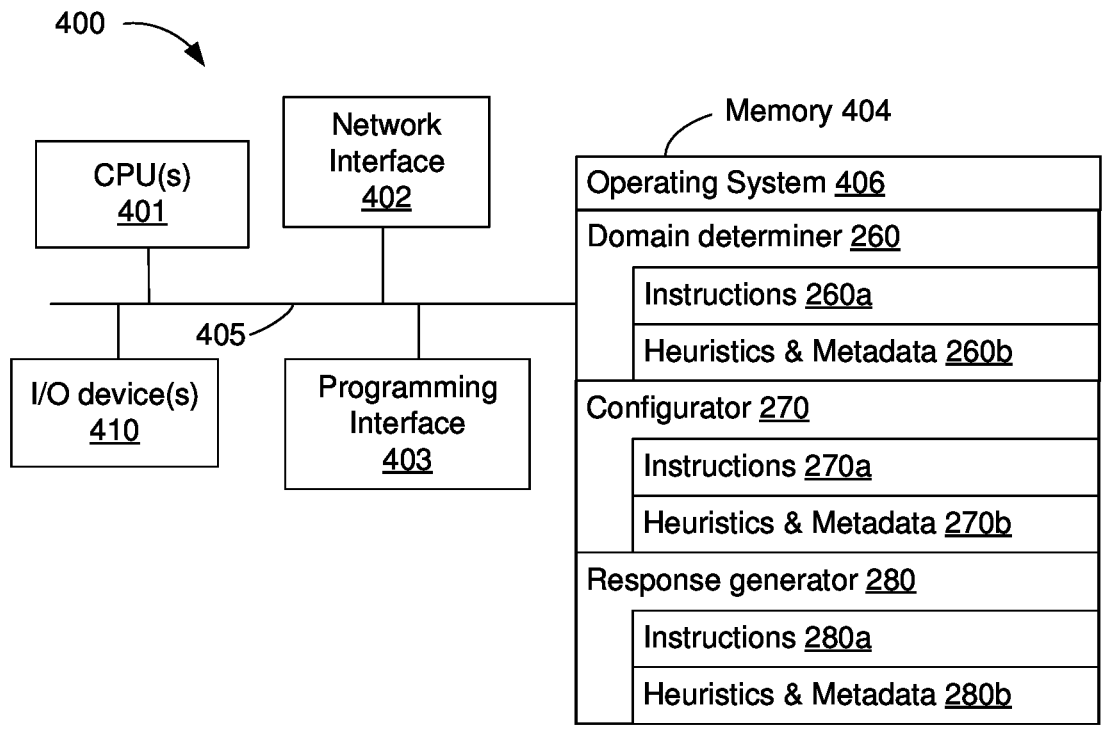
FIG. 4 is a block diagram of a device that provides domain-specific responses in accordance with some implementations.

FIG. 4 is a block diagram of a device 400 that provides domain-specific responses in accordance with some implementations. In some implementations, the device 400 implements the device 20 shown in FIGS. 1A-1I, and/or the virtual agent 200 shown in FIGS. 1A-2. In some implementations, the device 400 is implemented by a server or a cloud computing platform. While certain specific features are illustrated, those of ordinary skill in the art will appreciate from the present disclosure that various other features have not been illustrated for the sake of brevity, and so as not to obscure more pertinent aspects of the implementations disclosed herein. To that end, as a non-limiting example, in some implementations, the device 400 includes one or more processing units (CPUs) 401, a network interface 402, a programming interface 403, a memory 404, one or more input/output (I/O) devices 410, and one or more communication buses 405 for interconnecting these and various other components.

In some implementations, the network interface 402 is provided to, among other uses, establish and maintain a metadata tunnel between a cloud hosted network management system and at least one private network including one or more compliant devices. In some implementations, the one or more communication buses 405 include circuitry that interconnects and controls communications between system components. The memory 404 includes high-speed random access memory, such as DRAM, SRAM, DDR RAM or other random access solid state memory devices, and may include non-volatile memory, such as one or more magnetic disk storage devices, optical disk storage devices, flash memory devices, or other non-volatile solid state storage devices. The memory 404 optionally includes one or more storage devices remotely located from the one or more CPUs 401. The memory 404 comprises a non-transitory computer readable storage medium.

In some implementations, the memory 404 or the non-transitory computer readable storage medium of the memory 404 stores the following programs, modules and data structures, or a subset thereof including an optional operating system 406, the domain determiner 260, the configurator 270, and the response generator 280. In various implementations, the device 400 performs the method 300 shown in FIG. 3.

As described herein, in various implementations, the domain determiner 260 determines a domain that a user is interested in learning about. To that end, the domain determiner 260 includes instructions 260a, and heuristics and metadata 260b.

As described herein, in various implementations, the configurator 270 determines configuration values for the response generator 280 in order to configure the virtual agent to operate as a domain-specific virtual agent. To that end, the configurator 270 includes instructions 270a, and heuristics and metadata 270b.

As described herein, in various implementations, the response generator 280 generates responses to queries based on information provided by a set of content items associated with the domain that the user is interested in learning about. To that end, the response generator 280 includes instructions 280a, and heuristics and metadata 280b.

In various implementations, the one or more I/O devices 410 include one or more sensors. In some implementations, the one or more I/O devices 410 include an audio sensor (e.g., a microphone) for receiving an audible signal (e.g., an audible signal that corresponds to the query 50 shown in FIGS. 1C and 2). In some implementations, the one or more I/O devices 410 include a display for displaying a response (e.g., the response 60 shown in FIGS. 1C and 2). In some implementations, the one or more I/O devices 410 include a speaker for outputting an audible signal that corresponds to a response.

While various aspects of implementations within the scope of the appended claims are described above, it should be apparent that the various features of implementations described above may be embodied in a wide variety of forms and that any specific structure and/or function described above is merely illustrative. Based on the present disclosure one skilled in the art should appreciate that an aspect described herein may be implemented independently of any other aspects and that two or more of these aspects may be combined in various ways. For example, an apparatus may be implemented and/or a method may be practiced using any number of the aspects set forth herein. In addition, such an apparatus may be implemented and/or such a method may be practiced using other structure and/or functionality in addition to or other than one or more of the aspects set forth herein.

It will also be understood that, although the terms "first", "second", etc. may be used herein to describe various elements, these elements should not be limited by these terms. These terms are only used to distinguish one element from another. For example, a first node could be termed a second node, and, similarly, a second node could be termed a first node, which changing the meaning of the description, so long as all occurrences of the "first node" are renamed consistently and all occurrences of the "second node" are renamed consistently. The first node and the second node are both nodes, but they are not the same node.

The terminology used herein is for the purpose of describing particular implementations only and is not intended to be limiting of the claims. As used in the description of the implementations and the appended claims, the singular forms "a", "an", and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting", that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

What is claimed is:

1. A method comprising:
   at a device including a non-transitory memory and a processor coupled with the non-transitory memory:
      obtaining, by a multidomain virtual agent, contextual data that indicates a context of the device or a user of the device, wherein the multidomain virtual agent provides voice search capability for a plurality of pharmaceutical articles;
      determining, based on the contextual data, a user interest value indicative of a first pharmaceutical article, from the plurality of pharmaceutical articles, that the user is interested in learning about, wherein the first pharmaceutical article is associated with a set of media content items that provide information regarding the first pharmaceutical article;
      transforming the multidomain virtual agent into a domain-specific virtual agent that provides voice search capability for the first pharmaceutical article and not a remainder of the plurality of pharmaceutical articles by setting a configuration parameter of the multidomain virtual agent to a configuration value that is based on the first pharmaceutical article indicated by the user interest value; and
      after setting the configuration parameter of the multidomain virtual agent, generating, by the domain-specific virtual agent, a response to a query based on the information provided by the set of media content items associated with the first pharmaceutical article.

2. The method of claim 1, wherein setting the configuration parameter of the multidomain virtual agent to the configuration value comprises:
   biasing the multidomain virtual agent to use the set of media content items associated with the first pharmaceutical article to generate responses to queries while the configuration parameter is set to the configuration value that is based on the first pharmaceutical article indicated by the user interest value.

3. The method of claim 1, wherein setting the configuration parameter of the multidomain virtual agent to the configuration value comprises:
   utilizing the set of media content items associated with the first pharmaceutical article to train the multidomain virtual agent.

4. The method of claim 1, wherein setting the configuration parameter of the multidomain virtual agent to the configuration value comprises:
   loading a response generation model that has been trained using the set of media content items associated with the first pharmaceutical article.

5. The method of claim 4, wherein loading the response generation model comprises:
   selecting the response generation model from a plurality of response generation models that have been trained using respective sets of media content items associated with corresponding ones of the plurality of pharmaceutical articles.

6. The method of claim 1, wherein the configuration value refers to a set of entities that are extracted from the set of media content items associated with the first pharmaceutical article.

7. The method of claim 1, wherein setting the configuration parameter comprises:
   setting the configuration parameter to the configuration value for a particular amount of time.

8. The method of claim 1, wherein setting the configuration parameter comprises:
   setting the configuration parameter to the configuration value for a time duration of a calendar event that is related to the first pharmaceutical article.

9. The method of claim 1, wherein setting the configuration parameter comprises:
   setting the configuration parameter to the configuration value while a user profile is associated with the first pharmaceutical article; and
   resetting the configuration parameter to a default value in response to detecting that the user profile is not associated with the first pharmaceutical article.

10. The method of claim 1, wherein the first pharmaceutical article includes a pharmaceutical drug or a medical device that treats a particular medical condition; and
   wherein determining the user interest value comprises:
      obtaining, from a navigation application, a destination location that the navigation application is providing navigational directions to; and
      setting the user interest value to a value corresponding to the first pharmaceutical article in response to determining that the destination location corresponds to a geographical location where a healthcare provider treats the particular medical condition.

11. The method of claim 1, wherein generating the response comprises:
performing entity tagging by matching terms in the query with entities that are specific to the first pharmaceutical article and are included in a set of entities referenced by the configuration value.

12. The method of claim 1, wherein generating the response comprises:
determining an intent associated with the query by matching terms in the query with intents that are specific to the first pharmaceutical article and are included in a set of intents referenced by the configuration value; and
synthesizing the response in order to satisfy the intent associated with the query.

13. The method of claim 1, further comprising:
determining a second user interest value indicative of a second pharmaceutical article, from the plurality of pharmaceutical articles, that the user is interested in learning about;
transforming the domain-specific virtual agent into a second domain-specific virtual agent that provides voice search capability for the second pharmaceutical article by setting the configuration parameter to a second configuration value that is based on the second pharmaceutical article; and
after setting the configuration parameter to the second configuration value, generating, by the second domain-specific virtual agent, a second response to a second query based on information provided by a second set of media content items associated with the second pharmaceutical article.

14. The method of claim 1, wherein the first pharmaceutical article includes a pharmaceutical drug or a medical device that treats a particular medical condition; and
wherein determining the user interest value comprises:
obtaining a current geographical location of the device;
determining a distance between the current geographical location of the device and a geographical location where a healthcare provider treats the particular medical condition; and
setting the user interest value to a value corresponding to the first pharmaceutical article in response to the distance being less than a threshold distance.

15. The method of claim 1, wherein the first pharmaceutical article includes a pharmaceutical drug or a medical device that treats a particular medical condition; and
wherein determining the user interest value comprises:
obtaining calendar data indicative of a future calendar event that is scheduled at a time that is within a threshold time duration of a current time; and
setting the user interest value to a value corresponding to the first pharmaceutical article in response to determining that the future calendar event corresponds to a meeting with a healthcare provider that treats the particular medical condition.

16. The method of claim 1, wherein determining the user interest value comprises:
obtaining user profile data indicative of a set of one or more pharmaceutical articles that a user of the device is responsible for discussing with healthcare providers; and
setting the user interest value to a value corresponding to the first pharmaceutical article in response to the set of one or more pharmaceutical articles including the first pharmaceutical article.

17. The method of claim 1, wherein determining the user interest value comprises:
obtaining user profile data indicative of a subset of the plurality of pharmaceutical articles that the user of the device is responsible for discussing with healthcare providers;
determining respective user comprehension scores for the subset of the plurality of pharmaceutical articles, wherein the respective user comprehension scores indicate corresponding user comprehension levels of the user with regards to information related to the subset of the plurality of pharmaceutical articles; and
setting the user interest value to a value corresponding to the first pharmaceutical article in response to the first pharmaceutical article being associated with a lowest one of the respective user comprehension scores.

18. A non-transitory memory storing one or more programs, which, when executed by one or more processors of a device, cause the device to:
obtain, by a multidomain virtual agent, contextual data that indicates a context of the device or a user of the device, wherein the multidomain virtual agent provides voice search capability for a plurality of pharmaceutical articles;
determine, based on the contextual data, a user interest value indicative of a first pharmaceutical article, from the plurality of pharmaceutical articles, that the user is interested in learning about, wherein the first pharmaceutical article is associated with a set of media content items that provide information regarding the first pharmaceutical article;
transform the multidomain virtual agent into a domain-specific virtual agent that provides voice search capability for the first pharmaceutical article and not a remainder of the plurality of pharmaceutical articles by setting a configuration parameter of the multidomain virtual agent to a configuration value that is based on the first pharmaceutical article indicated by the user interest value; and
after setting the configuration parameter of the multidomain virtual agent, generate, by the domain-specific virtual agent, a response to a query based on the information provided by the set of media content items associated with the first pharmaceutical article.

19. A device comprising:
one or more processors;
a non-transitory memory; and
one or more programs stored in the non-transitory memory, which, when executed by the one or more processors, cause the device to:
obtain, by a multidomain virtual agent, contextual data that indicates a context of the device or a user of the device, wherein the multidomain virtual agent provides voice search capability for a plurality of pharmaceutical articles;
determine, based on the contextual data, a user interest value indicative of a first pharmaceutical article, from the plurality of pharmaceutical articles, that the user is interested in learning about, wherein the first pharmaceutical article is associated with a set of media content items that provide information regarding the first pharmaceutical article;
transform the multidomain virtual agent into a domain-specific virtual agent that provides voice search capability for the first pharmaceutical article and not a remainder of the plurality of pharmaceutical articles by setting a configuration parameter of the multidomain virtual agent to a configuration value that is based on the first pharmaceutical article indicated by the user interest value; and after setting the configuration parameter of the multidomain virtual agent, generate, by the domain-specific virtual agent, a response to a query based on the information provided by the set of media content items associated with the first pharmaceutical article.

20. The non-transitory memory of claim 18, wherein setting the configuration parameter of the multidomain virtual agent to the configuration value comprises:

utilizing the set of media content items associated with the first pharmaceutical article to train the multidomain virtual agent.

21. The non-transitory memory of claim 18, wherein setting the configuration parameter comprises:

setting the configuration parameter to the configuration value for a particular amount of time.

22. The device of claim 19, wherein setting the configuration parameter of the multidomain virtual agent to the configuration value comprises:

loading a response generation model that has been trained using the set of media content items associated with the first pharmaceutical article.

23. The device of claim 19, wherein setting the configuration parameter comprises:

setting the configuration parameter to the configuration value for a time duration of a calendar event that is related to the first pharmaceutical article.

* * * * *